(12) United States Patent
Ratcliffe et al.

(10) Patent No.: US 7,763,732 B2
(45) Date of Patent: Jul. 27, 2010

(54) INDOLE DERIVATIVES

(75) Inventors: Paul David Ratcliffe, Newhouse (GB); Julia Adam-Worrall, Newhouse (GB); Angus John Morrison, Newhouse (GB); Stuart John Francis, Newhouse (GB); Takao Kiyoi, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/506,579

(22) Filed: Aug. 18, 2006

(65) Prior Publication Data

US 2007/0082931 A1     Apr. 12, 2007

Related U.S. Application Data

(60) Provisional application No. 60/710,805, filed on Aug. 24, 2005.

(51) Int. Cl.
*C07D 285/08*     (2006.01)
*C07D 271/10*     (2006.01)
*C07D 211/06*     (2006.01)

(52) U.S. Cl. .................. 546/201; 548/128; 548/143

(58) Field of Classification Search ................ None
See application file for complete search history.

(56) References Cited

U.S. PATENT DOCUMENTS

| 4,939,138 A | 7/1990 | D'Ambra et al. ............ 514/218 |
| 7,655,645 B2 | 2/2010 | Adam |
| 2007/0142446 A1* | 6/2007 | Adam-Worrall et al. ..... 514/362 |

FOREIGN PATENT DOCUMENTS

| WO | WO 01/58869 A2 | 8/2001 |
| WO | WO 01/58869 A3 | 8/2001 |
| WO | WO 02/36590 A1 | 5/2002 |
| WO | WO 02/060447 A1 | 8/2002 |
| WO | WO 04/000832 A1 | 12/2003 |
| WO | WO 2005/058327 A1 | 6/2005 |
| WO | WO 2005/089754 A1 | 9/2005 |
| WO | WO 2007/023143 A1 | 3/2007 |
| WO | WO 2008/101995 A1 | 8/2008 |

OTHER PUBLICATIONS

Tarzia et al., "Synthesis and structure-activity relationships of a series of pyrrole cannabinoid receptor agonists", bioorganic&medicinal chemistry 2003, 11, 3965-3973.*
Huffman et al., "structure-activity relationship for 1-alkyl-3-(1-naphthoyl)indoles at the cannabinoid CB1 and CB2 receptors: steric and electronic effects of naphthoyl substituents. New highly selective CB2 receptor agonists", bioorganic&medicinal chemistry, 13, 2005, 89-112.*
Hacks Chemical Dictionary, Fourth Edition, Julius Grant, 1972, p. 203.*
Robinson, B., "Recent Studies on the Fischer Indole Synthesis," Chem. Rev., vol. 63 (1963) pp. 227-250.
Jutz, C., "The Vilsmeier-Haack-Arnold Acylations. C-C Bond-Forming Reactions of Chloromethyleniminium Ions," Adv. Org. Chem., vol. 9, Part I (1976) pp. 225-342.
Howlett, A. C. et al., "International Union of Pharmacology. XXVII. Classification of Cannabinoid Receptors," Pharmacological Reviews, vol. 54 (2002) pp. 161-202.
Iversen, L. et al., "Cannabinoids: a real prospect for pain relief?," Current Opinion in Pharmacology 2 (2002) pp. 50-55.
Eissenstat, M. A. et al., "Aminoalkylindoles: Structure-Activity Relationships of Novel Cannabinoid Mimetics," J. Med. Chem., vol. 38 (1995) pp. 3094-3105.
Adam, J. et al., "Recent advances in the cannabinoids," Expert Opin. Ther. Patents, vol. 12, No. 10 (2002) pp. 1475-1489.
Wijnggaarden, I. et al., "Development of High-Affinity 5-HT$_3$ Receptor Antagonists. Structure-Affinity Relationships of Novel 1,7-Annelated Indole Derivatives. 1," J. Med. Chem. vol. 36 (1993) pp. 3693-3699.
Hwu, J. R. et al., "Novel Methods for the Synthesis of Functionalized Indoles from Arylhydroxylamines and Activated Acetylenes," J. Org. Chem., vol. 59 (1994) pp. 1577-1582.
Miyaura, N. et al., "Palladium-Catalyzed Cross-Coupling Reactions of Organoboron Compounds," Chem. Rev., vol. 95 (1995) pp. 2457-2483.
Stratowa, C. et al., "Use of a luciferase reporter system for characterizing G-protein-linked receptors," Current Opinion in Biotechnology, vol. 6 (1995) pp. 574-581.
Yaksh, T. et al., "An automated flinch detecting system for use in the formalin nociceptive bioassay," J. Appl. Physiol., vol. 90 (2001) pp. 2386-2402.
International Search Report for Application No. PCT/EP2005/050833 dated Jun. 21, 2005.
International Preliminary Examination Report on Patentability of International Application No. PCT/EP2005/050833 dated Jan. 31, 2006.

(Continued)

*Primary Examiner*—Rei-Tsang Shiao
*Assistant Examiner*—Sun Jae Y Loewe
(74) *Attorney, Agent, or Firm*—Susan L. Hess

(57) ABSTRACT

Disclosed herein are indole derivatives of the formula (I)

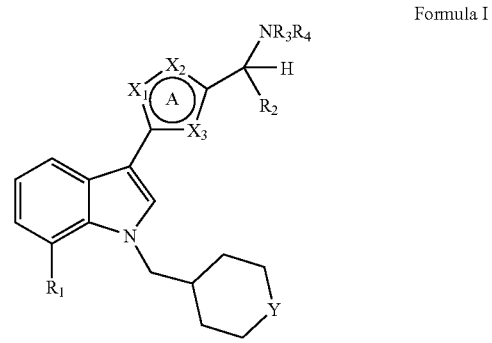

Formula I wherein each of the substitutents is given the definition as set forth in the specification and claims. Also disclosed are pharmaceutical compositions containing the indole derivatives and use of the derivatives for the treatment of pain.

16 Claims, No Drawings

OTHER PUBLICATIONS

Written Opinion of International Application No. PCT/EP2005/050833 dated Jun. 21, 2006.

Huffman et al., "structure activity relationship for 1-alkyl-3-(1-naphthoyl)indoles at the cannabinoid CB1 and CB2 receptors: steric and electronic effects of naphthoyl substituents. New highly selective CB2 receptor agonists," bioorganic&medicinal chemistry, 13. 2005, 89-112.

Luly, J. R. et al., "A Synthesis of Protected Aminoalkyl Epoxides from Amino Acids," J. Org. Chem., vol. 52 (1987) pp. 1487-1492.

Tarzia et al., "Synthests and structure-activity relationships of a series of pyrrole cannabinoid receptor agonists," bioorganic & medicinal chemistry 2003, 11, 3965-3973.

PCT International Search Report dated Apr. 23, 2008 and Written Opinion dated Apr. 23, 2008 for International Application No. PCT/EP2008/052141.

* cited by examiner

INDOLE DERIVATIVES

The present invention relates to indole derivatives, to pharmaceutical compositions comprising the same and to the use of these indole derivatives in therapy, especially in the treatment of pain.

Pain treatment is often limited by the side effects of currently available medication. For moderate to severe pain, opioids are widely used. These agents are cheap and effective but suffer from serious and potentially life-threatening side effects, most notably respiratory depression and muscle rigidity. In addition, the doses of opioids which can be administered are limited by nausea, emesis, constipation, pruritis and urinary retention, often resulting in patients electing to receive sub-optimal pain control rather than suffer these distressing side effects. Furthermore, these side effects often result in patients requiring extended hospitalisation. Opioids are highly addictive and are scheduled drugs in many territories. There is therefore a demand for new analgesics that have an improved side effect profile compared to currently used products, at equi-analgesic doses.

Evidence is accumulating that cannabinoid agonists have potential as analgesic and anti-inflammatory agents. Two types of cannabinoid receptors are implicated, the cannabinoid CB1 receptor, which is located primarily in the central nervous system but which is also expressed by peripheral neurones and to a lower extent in other peripheral tissues, and the cannabinoid CB2 receptor, which is mostly located in immune cells (Howlett, A. C. et al, International Union of Pharmacology. XXVII. Classification of Cannabinoid Receptors. *Pharmacol. Rev.* 54, 161-202, 2002). While the CB2 receptor has been implicated in modulating the immune and anti-inflammatory response of cannabinoids, cannabinoid receptor agonists, especially those acting at the CB1 receptor have been suggested as useful in the treatment of pain (see Iversen, L. and Chapman, V. *Current Opinion in Pharmacology* 2, 50-55, 2002 and references therein).

WIN 55,212-2, the mesylate salt of (R)-(+)-[2,3-dihydro-5-methyl-[(morpholinyl) methyl]pyrrolo[1,2,3-de]-1,4-benzoxazinyl]-(1-naphthalenyl)methanone was disclosed in U.S. Pat. No. 4,939,138 (Sterling Drug Inc.) as an analgesic agent. The compound is the prototype of aminoalkylindoles (Eissenstat, M. A. et al, *J. Med. Chem.* 38, 3094-3105, 1995), which are potent cannabinoid CB1 receptor agonists that can produce antinociception with equivalent efficacy to morphine in animal models of acute pain, persistent inflammatory pain and neuropathic pain.

Key structural features of aminoalkylindoles having cannabimimetic properties (Adam, J. and Cowley, P. *Expert Opin. Ther. Patents,* 12, 1475-1489, 2002) are an aminoalkyl substituent at the 1-position of the indole moiety, and a further bulky substituent in the 3-position of the indole ring, such as exemplified by an aroyl group in the aminoalkylindoles disclosed in U.S. Pat. No. 4,939,138 (Sterling Drug Inc.) and in the more recent WO02060447 (University of Connecticut), or by a substituted amido-group in the compounds disclosed in WO0158869 (Bristol-Myers Squibb). Recently, 1-(aminoalkyl)indole derivatives having a substituted oxadiazol-5-yl ring at the 3-position were disclosed in WO0236590 (Amrad Operations PTY Ltd.) as cannabinoid receptor modulators and useful as analgesic agents.

In WO04000832 (Akzo Nobel N.V.) 1-[(indol-3-yl)carbonyl]piperazine derivatives are disclosed as analgesic agents which modulate the cannabinoid receptor.

There remains a need for cannabinoid agonists with improved properties, such as increased water solubility, for use as therapeutic agents.

To this end the present invention provides indole derivatives having the general Formula I

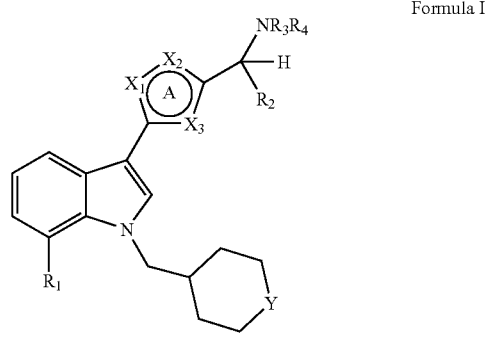

Formula I wherein

A represents a 5-membered aromatic heterocyclic ring, wherein $X_1$, $X_2$ and $X_3$ are independently selected from N, O, S and CR;

R, when present, is H, halogen or $(C_{1-4})$alkyl;

Y is $CH_2$, O, S or $SO_2$;

$R_1$ is $(C_{1-4})$alkyl, $(C_{1-4})$alkyloxy, CN or halogen;

$R_2$ is H or $(C_{1-4})$alkyl; or $R_2$ together with $R_3$ and the carbon and nitrogen atoms to which they are bonded form a 4-7 membered ring;

$R_3$ is H, $(C_{1-6})$alkyl or $(C_{3-7})$cycloalkyl, the alkyl groups being optionally substituted with OH, $(C_{1-4})$alkyloxy, $(C_{1-4})$alkylthio, $(C_{1-4})$alkylsulfonyl, CO—$NR_5R_6$, CO—$OR_7$, CN or halogen;

$R_4$ is CO—$NR_5R_6$, CO—$OR_7$, $SO_2$—R8, $SO_2$—$NR_9R_{10}$, or CO—$R_{11}$; or $R_4$ is $(C_{1-3})$alkyl, substituted with CO—$NR_5R_6$, CO—$OR_7$, $SO_2$—$R_8$, $SO_2$—$NR_9R_{10}$, NH—C—$R_{11}$, NH—$SO_2$—$R_{12}$, or two OH groups; and optionally further substituted with OH; or $R_4$ together with $R_3$ and the N to which they are bonded form a 4-8 membered ring optionally containing a further heteroatom selected from O, S and $SO_2$, the ring being substituted with $CH_2$—OH, CO—$NR_{13}R_{14}$, CO—$OR_7$, $SO_2$—$R_8$, $SO_2$—$NR_9R_{10}$, NH—CO—$R_{11}$ or NH—$SO_2$—$R_{12}$; or the ring being substituted with $(C_{1-3})$alkyl, substituted with NH—CO—$R_{11}$ or NH—$SO_2$—$R_{12}$;

$R_5$, when present, is H or $(C_{1-4})$alkyl, optionally substituted with OH, $(C_{1-4})$alkyloxy or $CONR_7R_8$;

$R_6$, when present, is H or $(C_{1-4})$alkyl; or $R_6$ together with $R_5$ and the N to which they are bonded form a 4-8 membered ring optionally containing a further heteroatom selected from O, S and $SO_2$, the ring being optionally substituted with OH;

$R_7$, when present, is H or $(C_{1-4})$alkyl;

$R_8$, when present, is $(C_{1-4})$alkyl or $(C_{3-7})$cycloalkyl, optionally substituted with OH or $(C_{1-4})$alkyloxy;

$R_9$, when present, is H or $(C_{1-4})$alkyl, optionally substituted with OH or $(C_{1-4})$alkyloxy;

$R_{10}$, when present, is H or $(C_{1-4})$alkyl;

$R_{11}$, when present, is H or $(C_{1-4})$alkyl, optionally substituted with OH or $(C_{1-4})$alkyloxy;

$R_{12}$, when present, is $(C_{1-4})$alkyl, optionally substituted with OH or $(C_{1-4})$alkyloxy;

$R_{13}$, when present, is H or $(C_{1-4})$alkyl, optionally substituted with OH, $(C_{1-4})$alkyloxy or $CONR_7R_8$;

$R_{14}$, when present, is H or $(C_{1-4})$alkyl; or $R_{14}$ together with the C atom to which the CO—$NR_{13}R_{14}$ group is bonded form a 5- or 6-membered spiro-ring;

with the proviso that when Y is $SO_2$, $R_4$ may further represent H, $(C_{1-6})$alkyl or $(C_{3-7})$cycloalkyl, the alkyl groups being optionally substituted with OH, $(C_{1-4})$alkyloxy, $(C_{1-4})$alkylthio, $(C_{1-4})$alkylsulfonyl, CN or halogen; or $R_3$ together with $R_4$ and the N to which they are bonded may form a 4-8 membered ring optionally containing a further heteroatom selected from O, S and $SO_2$ the ring being optionally substituted with OH; or a pharmaceutically acceptable salt thereof, as agonists of the cannabinoid CB1 receptor, which can be used in the treatment of pain such as for example peri-operative pain, chronic pain, neuropathic pain, cancer pain and pain and spasticity associated with multiple sclerosis.

In the definition of the indol derivatives of Formula I a broader scope is defined by way of a proviso in case Y has the meaning of $SO_2$. This proviso relates to the earlier description of related indole derivatives for which Y is $CH_2$, O or S, in the International Patent Application EP05/050833 (AKZO NOBEL N.V.), filed on Feb. 28, 2005.

The 5-membered aromatic heterocyclic ring A, as used in the definition of Formula I, represents a 5-membered aromatic heterocyclic ring, which contains 1-3 heteroatoms selected from N, O and S. This means that at least one of $X_1$, $X_2$ and $X_3$, used to define heterocycle A, cannot be CR. Representative heterocycles A are those derived from thiophene, furan, thiazole, thiadiazole, oxazole, oxadiazole and their isomers including isothiazole, isothiadiazole, isoxazole and isoxadiazole. Preferred heterocycles A are 1,2,4-oxadiazole ($X_1$ is N, $X_2$ is O, $X_3$ is N), 1,3,4-oxadiazole ($X_1$ is N, $X_2$ is N, $X_3$ is O), 1,2,4-thiadiazole ($X_1$ is N, $X_2$ is S, $X_3$ is N) and thiazole ($X_1$ is S, $X_2$ is CR, $X_3$ is N).

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

The term $(C_{1-4})$alkyl likewise means a branched or unbranched alkyl group having 1-6 carbon atoms, like hexyl, pentyl, butyl, isobutyl, tertiary butyl, propyl, isopropyl, ethyl and methyl.

The term $(C_{3-7})$cycloalkyl means a cycloalkyl group having 3-7 carbon atoms, like cycloheptyl, cyclohexyl, cyclopentyl, cyclobutyl and cyclopropyl.

In the terms $(C_{1-4})$alkyloxy, $(C_{1-4})$alkylthio and $(C_{1-4})$alkylsulfonyl, $(C_{1-4})$alkyl has the meaning as defined above.

The term halogen means F, Cl, Br or I.

In the definition of Formula I $R_2$ together with $R_3$ and the carbon and nitrogen atoms to which they are bonded may form a 4-7 membered ring. Examples of such saturated rings are azetidiny-2-yl, pyrolidin-2-yl, piperidin-2-yl and azepin-2-yl.

In the definition of Formula I $R_4$ together with $R_3$ and the N to which they are bonded may form a 4-8 membered ring, optionally containing a further heteroatom selected from O, S and $SO_2$. Examples of such rings are pyrrolidin-1-yl, piperi-din-1-yl, azepin-1-yl, morpholin-4-yl and thiomorpholin-4-yl. Preferred are pyrrolidin-1-yl, piperidin-1-yl and morpholin-4-yl.

In the definition of Formula I $R_6$ together with $R_5$ and the N to which they are bonded may form a 4-8 membered ring, optionally containing a further heteroatom selected from O, S and $SO_2$. Examples of such ring are pyrrolidin-1-yl, piperidin-1-yl, azepin-1-yl, morpholin-4-yl and thiomorpholin-4-yl. Preferred is morpholin-4-yl.

In the definition of the indol derivatives of Formula I there may be multiple occurrences of the substituents $R_5$, $R_6$, $R_7$ and $R_8$. For each occurrence the meaning is independently selected from the meanings as defined for each of the substituents.

There is a preference for indole derivatives according to Formula I, wherein R, when present, is H; Y is $CH_2$, O or $SO_2$; $R_2$ is H; or $R_2$ together with $R_3$ and the carbon atom to which they are bonded form a 5-membered ring.

Further preferred are the compounds according to Formula I wherein heterocycle A is 1,2,4-oxadiazole ($X_1$ is N, $X_2$ is O, $X_3$ is N), 1,2,4-thiadiazole ($X_1$ is N, $X_2$ is S, $X_3$ is N), thiazole ($X_1$ is S, $X_2$ is CR, $X_3$ is N) or 1,3,4-oxadiazole ($X_1$ is N, $X_2$ is N, $X_3$ is O). More preferred are the compounds wherein the heterocycle A represents 1,2,4-oxadiazole ($X_1$ is N, $X_2$ is O, $X_3$ is N) or 1,2,4-thiadiazole ($X_1$ is N, $X_2$ is S, $X_3$ is N), especially so when $R_3$ is $(C_{1-6})$alkyl optionally substituted with OH and $R_4$ is $SO_2$—$R_8$ or $(C_{1-3})$ alkyl, substituted with CO—$NR_5R_6$; or when $R_4$ together with $R_3$ and the N to which they are bonded form a 6-membered ring, the ring being substituted with CO—$NR_{13}R_{14}$.

Specifically preferred indole derivatives of the invention are:

7-chloro-3-[(5-{[4-(N-methyl)carboxamido]piperidin-1-yl}methyl)-([1,2,4]-thiadiazol-3-yl)]-1-(1,1-dioxo-hexahydro-thiopyran-4-yl)methyl-1H-indole;

7-chloro-3-[(5-{4-[(N-{2-hydroxy}ethyl)carboxamido]piperidin-1-yl}methyl)-([1,2,4]oxadiazol-3-yl)]-1-(tetrahydropyran-4-yl)methyl-1H-indole;

7-chloro-3-[(5-{[N-(carboxamido)methyl]-N-methylamino}methyl)-([1,2,4]oxadiazol-3-yl)]-1-(tetrahydropyran-4-yl)methyl-1H-indole;

7-chloro-3-({5-[(N{-[N-(carboxamido)methyl]carboxamido}methyl)-N-methyl-amino]methyl}-[1,2,4]oxadiazol-3-yl)-1-(tetrahydropyran-4-yl)methyl-1H-indole;

7-chloro-3-({5-[(N-{[N-(2-hydroxyethyl)]carboxamido}methyl)-N-methyl-amino]methyl}-[1,2,4]oxadiazol-3-yl)-1-(tetrahydropyran-4-yl)methyl-1H-indole;

7-chloro-3-({5-[(N-{2-hydroxy}ethyl)-(N-{methylsulfonyl})amino]methyl}-([1,2,4]-thiadiazol-3-yl))-1-(tetrahydropyran-4-yl)methyl-1H-indole;

7-ethyl-3-[(5-{4-[(N-{2-hydroxy}ethyl)carboxamido]piperidin-1-yl}methyl)-([1,2,4]-thiadiazol-3-yl)]-1-(tetrahydropyran-4-yl)methyl-1H-indole;

or a pharmaceutically acceptable salt thereof.

The indole derivatives of the invention may be prepared by methods known in the art of organic chemistry in general.

(Indol-3-yl) heterocycle derivatives of Formula I can for instance be prepared from compounds of Formula II where L is a leaving group, such as a halogen or alkylsulfonate group, by nucleophilic displacement of the leaving group with an amine of formula $NHR_3R_4$. Compounds of Formula II where L is an alkylsulfonate group can be prepared from compounds of Formula II where L is hydroxy, by reaction with an alkylsulfonyl halide in the presence of a base such as triethylamine.

(Indol-3-yl) heterocycles of Formula I can be prepared from compounds of Formula III by reductive amination, using an amine of formula NHR$_3$R$_4$ in the presence of a reducing agent such as sodium triacetoxyborohydride.

It is well known in the art that compounds of Formula II where L is hydroxy can be inter-converted with compounds of Formula III, by oxidation and reduction using suitable oxidising and reducing agents, as described in Burke D. S., Danheiser, R. L. *Handbook of Reagents for Organic Synthesis: Oxidising and Reducing agents* (Wiley: New York, 1999). Likewise, compounds of Formula II where L is hydroxy and R$_2$ is hydrogen, can be prepared from compounds of Formula IV where R$_{15}$ is hydrogen or (C$_{1-4}$)alkyl, by reduction using suitable reducing agents.

Formula II
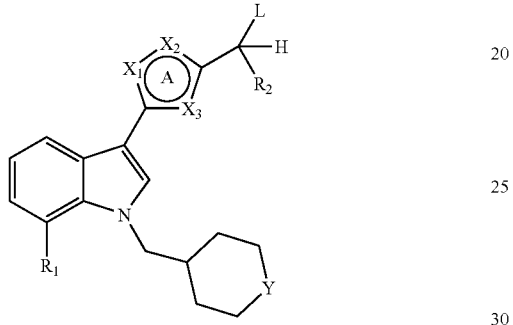

Formula III
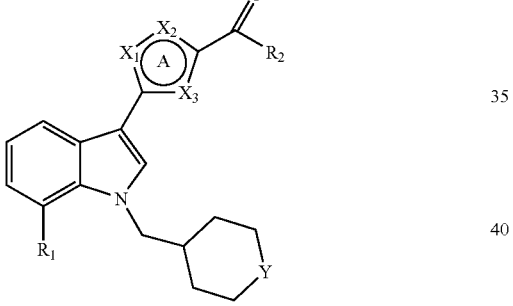

Formula IV
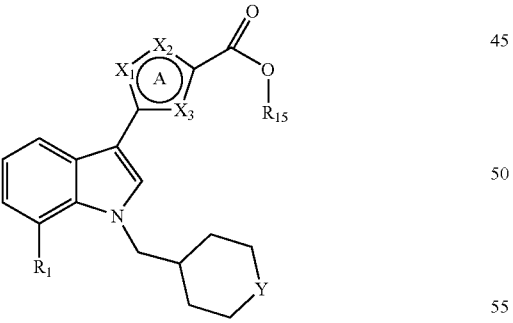

Compounds of Formula I, Formula II, Formula III or Formula IV can be prepared from compounds of Formula V to Formula XII inclusive, using methods well known in the art for constructing heterocyclic rings. Such methods are described in the general reference Katritzky, A. R.: *Comprehensive heterocyclic chemistry* (First Edition, Pergamon Press, 1984, see especially Volume 4, Part 3, *Five-membered rings with one oxygen, sulfur or nitrogen atom* and Volume 6, Part 4B, *Five-membered rings with two or more oxygen, sulfur or nitrogen atoms*).

Formula V
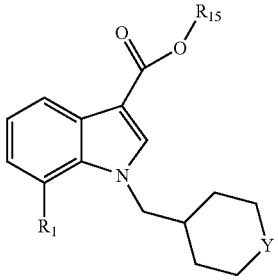

Formula VI
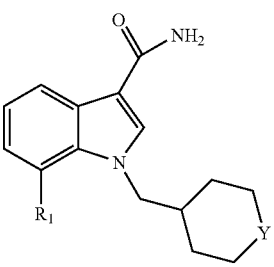

Formula
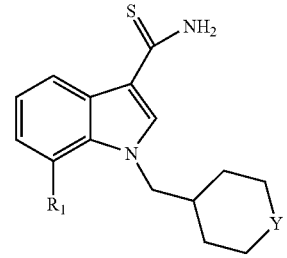

Formula VIII
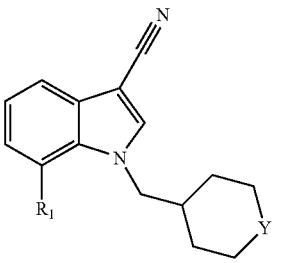

Formula IX
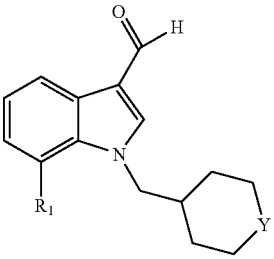

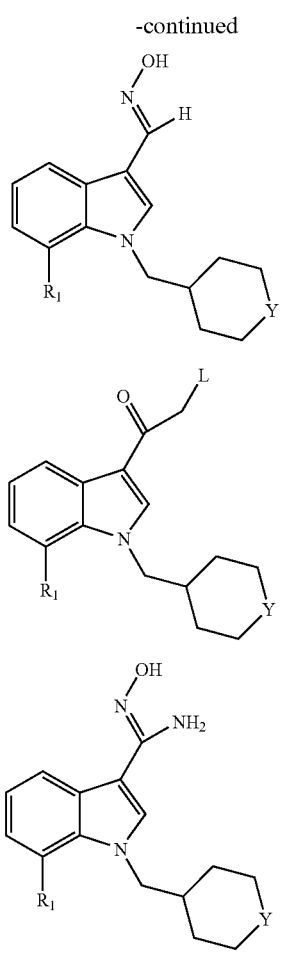

Formula X

Formula XI

Formula XII

Compounds of Formula V to Formula XII inclusive, wherein $R_1$, $R_2$, L and Y have the meanings as previously defined and $R_{15}$ is H or $(C_{1-4})$alkyl, can be prepared by literature procedures or modifications of literature procedures known to those persons skilled in the art.

For example, compounds of Formula VI can be prepared from compounds of Formula V, or activated derivatives thereof, by reaction with ammonia in a suitable solvent. Compounds of Formula VII can be prepared from compounds of Formula VI using thionation reagents, such as phosphorus pentasulfide or Lawesson's reagent. Alternatively, compounds of Formula VII can be prepared from compounds of Formula VII by reaction with thioacetamide in a solvent such as dimethylformamide. Compounds of Formula VII can be prepared from compounds of Formula VI by dehydration, for example using trifluoroacetic anhydride in the presence of a base such as triethylamine.

Compounds of Formula X can be prepared from compounds of Formula IX by reaction with hydroxylamine in a suitable solvent.

Compounds of Formula XI where L is $NH_2$ can be prepared from compounds of Formula V, or activated derivatives thereof, by reaction with cyanide anion to form an oxoacetonitrile, followed by reduction of the nitrile to a primary amine using a reducing agent, such as hydrogen gas in the presence of a catalyst such as palladium on charcoal.

Compounds of Formula XII can be prepared from compounds of Formula VIII by reaction with hydroxylamine in a suitable solvent.

Compounds of Formula V and compounds of Formula XI can be prepared by acylation of compounds of Formula XIII. For example, compounds of Formula V where $R_8$ is hydrogen can be prepared by acylation of compounds of Formula XIII using trifluoroacetic anhydride in a solvent such as dimethylformamide, followed by hydrolysis using aqueous sodium hydroxide at an elevated temperature. Compounds of Formula XI where L is chlorine can be prepared by acylation of compounds of Formula XIII using chloroacetyl chloride, in the presence of a base such as pyridine. Compounds of Formula IX can be prepared from compounds of Formula XIII by formylation, for example using the Vilsmeier reaction (for a review see Jutz, C. *Adv. Org. Chem.* 9, pt. 1, 225-342, 1976).

Alternatively, compounds of Formula V can be prepared from compounds of Formula XIV using procedures described by Wijngaarden et al, (*J. Med. Chem.* 36, 3693-3699, 1993) or Hwu et al, (*J. Org. Chem.* 59, 1577-1582, 1994) or modifications of these procedures.

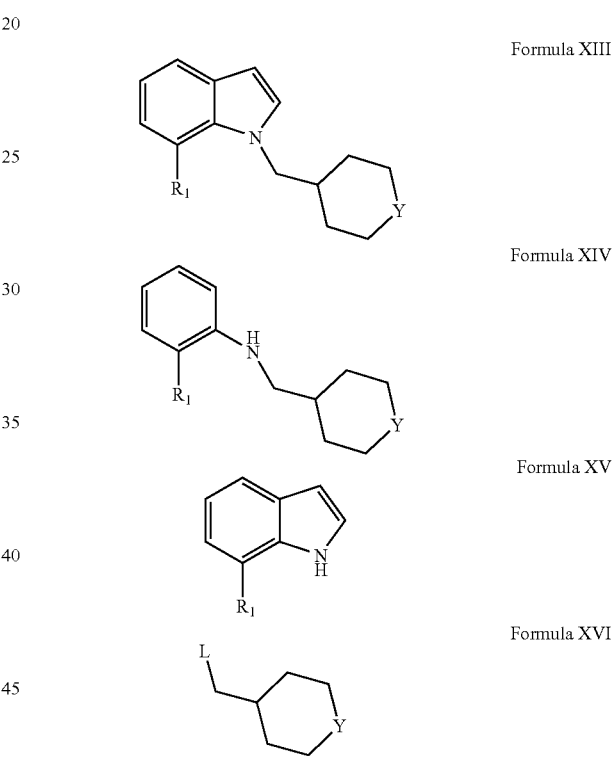

Formula XIII

Formula XIV

Formula XV

Formula XVI

Compounds of Formula XIII can be prepared by literature procedures or modifications of literature procedures known to those persons skilled in the art. For example, compounds of Formula XIII can be prepared by alkylation of compounds of Formula XV, by treatment with a base such as sodium hydride, followed by reaction with an alkylating agent of Formula XVI, where Y has the meaning as defined before and L is a leaving group, such as a halogen or alkylsulfonate group. Compounds of Formula XV can be obtained from commercial sources, prepared by literature procedures or modifications of literature procedures known to those persons skilled in the art. Alternatively, compounds of Formula XIII can be prepared from compounds of Formula XIV using the Fischer indole synthesis or modifications thereof (*Chem. Rev.* 69, 227-250, 1969).

Compounds of Formula XIV can be prepared by literature procedures or modifications of literature procedures known to those persons skilled in the art.

Compounds of Formula I, Formula II, Formula III or Formula IV may alternatively be prepared from compounds of Formula XVII using transition metal catalysed coupling reactions, as described in the general reference Hegedus, L. S. *Transition Metals in the Synthesis of Complex Organic Molecules* (Second Edition, University Science: Sausalito 1999).

For example, compounds of Formula III may be prepared by the reaction of compounds of Formula XVII, where $Y_1$ is halogen, with compounds of Formula XVIII, where $Y_2$ is a boronic acid or a boronic acid ester, using a Suzuki reaction (*Chem. Rev.* 95, 2457-2483, 1995) or a modification thereof.

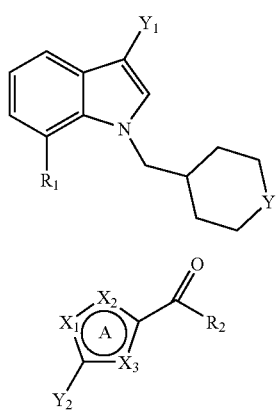

Formula XVII

Formula XVIII

Compounds of Formula XVII and compounds of Formula XVIII can be obtained from commercial sources, prepared by literature procedures or modifications of literature procedures known to those persons skilled in the art. For example, compounds of Formula XVII where $Y_1$ is bromine may be prepared by bromination of a compound of Formula XIII using bromine in a solvent such as dimethylformamide.

It will be appreciated by those persons skilled in the art that the indole nitrogen may be temporarily protected during the transformations described above using a protecting group, such as an arylsulfonyl group, to be deprotected and alkylated at a later stage in the synthesis. It will further be appreciated that such protecting groups may be used to modify the stability of intermediates and the reactivity of the indole ring towards electrophiles. Suitable protecting groups are described in Kocienski, P. J.: *Protecting Groups*, Thieme, Stuttgart; New York, 1994.

The skilled person will likewise appreciate that various (indol-3-yl) heterocycle derivatives of Formula I can be obtained by appropriate conversion reactions of functional groups corresponding to certain of the substituents $R_3$-$R_4$. For example, compounds of Formula I wherein $R_3$ or $R_4$ is a C1 to C6 linear, branched or cyclic alkyl group optionally substituted with hydroxyl, $(C_{1-4})$alkyloxy, $(C_{1-4})$alkylthio, $(C_{1-4})$-alkylsulfonyl, CO—$OR_7$, $CONR_8R_9$, halogen or cyano, can be prepared by the reaction of a compound of Formula I wherein $R_3$ or $R_4$ is hydrogen with a C1 to C6 alkyl halide or a functionalised C1 to C6 alkyl halide, in the presence of a base such as potassium carbonate.

Compounds of Formula I wherein $R_4$ is $CONR_5R_6$ or $COOR_7$ or $COR_{11}$ can be prepared by the reaction of a compound of Formula I wherein $R_4$ is hydrogen with a C1 to C4 acyl chloride, or isocyanate of anhydride or a functionalised C1 to C4 acyl chloride, in the presence of a base such as triethylamine.

Compounds of Formula I wherein $R_4$ is $SO_2R_8$ can be prepared by the reaction of a compound of Formula I wherein $R_4$ is hydrogen with a C1 to C4, or C3 to C7, alkyl, or cycloalkyl, sulfonyl chloride or a functionalised C1 to C4 alkyl sulfonyl chloride, in the presence of a base such as triethylamine.

Compounds of Formula I wherein $R_4$ is $SO_2NR_9R_{10}$ can be prepared by the reaction of a compound of Formula I wherein $R_4$ is hydrogen with sulfamide or a functionalised sulfamoyl chloride, in the presence of a base such as pyridine.

The indole derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereo-isomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a indole derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincoll Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The indole derivatives of the invention were found to be agonists of the CB1 receptor, as determined in a human CB1 reporter assay using CHO cells. Methods to determine receptor binding as well as in vitro biological activity of cannabinoid receptor modulators are well known in the art. In general, expressed receptor is contacted with the compound to be tested and binding or stimulation or inhibition of a functional response is measured.

To measure a functional response isolated DNA encoding the CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB1 expressing cell lines are well known in the art (Sambrook et al, Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed CB1 (or CB2) receptor may be used to measure binding of compound.

For measurement of binding radioactively or fluorescently labelled compounds may be used. The most widely used radiolabelled cannabinoid probe is [$^3$H]CP55940, which has approximately equal affinity for CB1 and CB2 binding sites.

Functional CB1 agonist activity may be measured by determining the second messenger response, such as for example measurement of receptor mediated changes in cAMP or MAPkinase pathways. Thus, such a method involves expression of the CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescent protein. The principles of such transactivation assays are well known in the art and are described e.g. in Stratowa, C., Himmler, A. and Czernilofsky, A. P., Curr. Opin. Biotechnol. 6, 574 (1995). For selecting active agonist compounds on the CB1 receptor the $EC_{50}$ value must be $<10^{-5}$ M, preferably $<10^{-7}$ M.

The compounds may be used as analgesic agents in the treatment of pain such as for example peri-operative pain, chronic pain, neuropathic pain, cancer pain and pain and spasticity associated with multiple sclerosis.

Cannabinoid agonists of the invention would also potentially be useful in the treatment of other disorders including multiple sclerosis, spasticity, inflammation, glaucoma, nausea and emesis, loss of appetite, sleep disturbances, respiratory disorders, allergies, epilepsy, migraine, cardiovascular disorders, neurodegenerative disorders, anxiety, traumatic brain injury and stroke.

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

General Methods

Microwave reactions were performed using an Emrys Optimizer™ (Personal Chemistry) unless otherwise stated.

Flash column chromatography was performed on silica gel.

Semi-preparative high pressure liquid chromatography (semi-prep. HPLC) was performed using the methods outlined below:

Method (i): Waters Xterra (RP18, 5 μm) 30 mm×100 mm; 10-100% acetonitrile-water over a 25 minute gradient; 25 ml/min; 0.1% trifluoroacetic acid buffer; detection by UV at 254 nm.

Method (ii): Waters Xterra (RP18, 5 μm) 30 mm×100 mm; 10-100% acetonitrile-water over a 25 minute gradient; 25 ml/min; 5 mM ammonium bicarbonate buffer, adjusted to pH 10 with ammonia; detection by UV at 254 nm.

$^1$H NMR coupling constants are given in Hz.

Preparation of Intermediates

I: Toluene-4-sulfonic acid tetrahydropyran-4-ylmethyl ester intermediate p-Toluenesulfonyl chloride (29.8 g, 157 mmol) was added portionwise to a mixture of tetrahydro-2H-pyran-4-yl-methanol (20.0 g, 172 mmol) and pyridine (25.2 ml, 313 mmol) in dichloromethane (200 ml). The mixture was stirred at room temperature for 17 h, then quenched with aqueous hydrochloric acid (2 M; 100 ml). The layers were separated and the aqueous layer extracted with dichloromethane (2×100 ml). The organic layers were combined and concentrated in vacuo. Recrystallisation from dichloromethane: n-heptane (5:1) afforded toluene-4-sulfonic acid tetrahydro-pyran-4-ylmethyl ester. The mother liquors were further purified by silica gel column chromatography eluting with 50% dichloromethane in n-heptane to yield a further quantity of toluene-4-sulfonic acid tetrahydro-pyran-4-ylmethyl ester (total yield 41.6 g, 154 mmol).

II: Toluene-4-sulfonic acid 1,1-dioxo-hexahydro-1-thiopyran-4-ylmethyl ester intermediate

Step A: Tetrahydro-thiopyran-4-carbonitrile

A mixture of tetrahydro-thiopyran-4-one (75 g, 646 mmol) and toluenesulfonyl-methyl isocyanide (138.6 g, 710 mmol) in dimethoxyethane (2.5 L) was cooled to 0° C. and a solution of potassium tert-butoxide (145 g, 1.29 mol) in tert-butanol (1.3 L) added dropwise. The mixture was then allowed to warm to room temperature and stirred for 3 h before dilution with diethylether (3 L), washing with sat'd sodium bicarbonate (2×1.5 L) and drying over magnesium sulfate. Removal of the solvent in vacuo gave tetrahydro-thiopyran-4-carbonitrile as a pale brown oil (88.3 g, 646 mmol).

Step B: Tetrahydro-thiopyran-4-carboxylic acid

A solution of tetrahydro-thiopyran-4-carbonitrile (646 mmol), in ethanol (600 ml) was added in one portion to a rapidly stirring mixture of sodium hydroxide (258.4 g, 6.46 mol) in water (1.1 L). The mixture was then heated to 90° C. for 2 h, cooled to 0° C. and the pH adjusted to 2 with conc. hydrochloric acid solution. The ethanol was then removed in vacuo and the suspension extracted into dichloromethane (3×1 L). The combined organic extracts were then dried over magnesium sulfate and evaporated in vacuo to give tetrahydro-thiopyran-4-carboxylic acid as a brown solid (96 g, 646 mmol).

Step C: (Tetrahydro-thiopyran-4-yl)-methanol

A solution of borane dimethylsulfide complex (73.5 ml, 775 mmol) in anhydrous tetrahydrofuran (1.5 L) was treated dropwise over 15 min with a solution of tetrahydro-thiopyran-4-carboxylic acid (646 mmol) in anhydrous tetrahydrofuran (300 ml). The mixture was then heated to 70° C. for 2 h, cooled to room temperature and quenched by dropwise addition of water until effervescence ceased. A further portion of water (500 ml) was then added and the tetrahydrofuran removed in vacuo. The residue was then acidified with dilute hydrochloric acid solution and extracted into dichloromethane (3×500 ml). The combined organic layers were then dried over sodium sulfate and the solvent removed in vacuo to give (tetrahydro-thiopyran-4-yl)-methanol as a brown oil (90.2 g, 646 mmol).

Step D: (1,1-Dioxo-hexahydro-1-thiolpyran-4-yl)-methanol

A solution of sodium periodate (304 g, 1.42 mol) in water (3 L) was treated with a solution of (tetrahydro-thiopyran-4-yl)-methanol in methanol (1.7 L) and the mixture heated to 60° C. for 3 h. Sodium periodate (10 g) was then added and heating continued for a further 1 h before removal of all volatiles in vacuo. The resulting granular residue was then shaken with succesive portions of diethyl ether (2×500 ml), dichloromethane (2×500 ml) and 50% (v/v) dichloromethane in methanol (2×500 ml). The remaining residue was then treated to a continous extraction using dichloromethane for 18 h and the solvent combined with the earlier solvent extractions, dried over sodium sulfate and evaporated in vacuo to give (1,1-dioxo-hexahydro-1-thiopyran-4-yl)-methanol as an orange oil (106.2 g, 646 mmol) which crystallised on standing.

Step E: Toluene-4-sulfonic acid 1,1-dioxo-hexahydro-1-thiopyran-4-ylmethyl ester A solution of (1,1-dioxo-hexahydro-1-thiopyran-4-yl)-methanol (105 g, 640 mmol), pyridine (155 ml, 1.92 mol) and 4-dimethylaminopyridine (2.5 g, 20.5 mmol) in chloroform (1.5 L) was treated portionwise with p-toluenesulfonyl chloride (244 g, 1.28 mol) over 15 mins. The mixture was the stirred for 72 h, washed with water (2×1 L), saturated sodium chloride solution (1 L) and dried over sodium sulfate. The organic solvent was removed in vacuo and the oily residue shaken with 60% (v/v) n-heptane in ethyl acetate to give a brown solid on filtration. This was dissolved in the minimum dichloromethane, passed through a celite pad eluting with ethyl acetate (4 L). The solvent was then removed in vacuo until the solution volume was 750 ml and n-heptane (1.5 L) added. The resulting suspension was then filtered to give the title compound as a sandy solid (130 g, 408 mmol). $^1$H NMR (400 MHz, CDCl$_3$): 1.80-2.00 (3H, m), 2.07-2.15 (2H, m), 2.46 (s, 3H), 2.90-3.09 (m, 4H), 3.90 (2H, d, J 6.3), 7.36 (2H, d, J 8.1) and 7.78 (2H, d, J 8.2).

EXAMPLE 1

7-Chloro-3-({5-[N-(morpholin-1-ylcarboxamido) methyl]aminomethyl}-([1,2,4]-thiadiazol-3-yl))-1-(tetrahydropyran-4-yl)methyl-1H-indole, hydrochloride salt

Step A: 7-Chloro-1H-indole-3-carboxylic acid

A solution of 7-chloroindole (7.1 g, 47.0 mmol) in dimethylformamide (60 ml) was cooled to 5° C. under nitrogen and trifluoroacetic anhydride (7.6 ml, 54.0 mmol) was added over 10 mins, maintaining the temperature below 10° C. The mixture was stirred at 5-10° C. for 2 h, then poured into water (600 ml). The resulting suspension was stirred for 15 mins and the 7-chloro-3-[(trifluoromethyl)carbonyl]-1H-indole precipitate was filtered off, washing with water to neutrality. The damp solid was suspended in 4 M aqueous sodium hydroxide (500 ml) and heated to reflux with stirring for 1 h. The mixture was cooled and washed with diethyl ether (2×100 ml). The aqueous phase was then acidified to pH 1 using 5 M hydrochloric acid and the resulting fine precipitate filtered off, washed with water to neutrality and dried to afford 7-chloro-1H-indole-3-carboxylic acid as a pink solid (7.5 g, 38.0 mmol).

Step B: 1-(Tetrahydropyran-4-yl)methyl-7-chloro-1H-indole-3-carboxylic acid

To a solution of 7-chloro-1H-indole-3-carboxylic acid (7.5 g, 38.0 mmol) in dimethylformamide (100 ml) at 10° C. under nitrogen was added sodium hydride (60% dispersion in mineral oil, 3.1 g, 76.0 mmol) portionwise over 10 mins, maintaining the temperature below 15° C. The cooling bath was removed and the suspension stirred for 90 mins. Toluene-4-sulfonic acid tetrahydropyran-4-ylmethylester (14.6 g, 53.0 mmol) was added. The mixture was heated at 50° C. with stirring for 6 h. Dimethylformamide was removed by evaporation and the residue was dissolved in water (500 ml). The emulsion was washed with dichloromethane (2×100 ml). The aqueous phase was acidified to pH 1 using 5 M hydrochloric acid and the precipitate filtered off, washed with water to neutrality and dried to afford 1-(tetrahydropyran-4-yl)methyl-7-chloro-1H-indole-3-carboxylic acid (15.0 g, 51.0 mmol) as a white solid.

Step C: 1-(Tetrahydropyran-4-yl)methyl-7-chloro-1H-indole-3-carboxylic acid amide Oxalyl chloride (9.0 ml, 102 mmol) was added dropwise to a mixture of 1-(tetrahydropyran-4-yl)methyl-7-chloro-1H-indole-3-carboxylic acid (15.0 g, 51.0 mmol) and dichloromethane (300 ml) under ice-water cooling and the resulting mixture was stirred at room temperature for 18 h. Dichloromethane and excess oxalyl chloride were removed by evaporation and the obtained residue was mixed with dichloromethane (300 ml). Aqueous ammonia solution (200 ml) was added, followed by potassium carbonate (13.5 g, 102 mmol). The resulting mixture was stirred for 1 h. The precipitate was filtered off and dried to afford 1-(tetrahydropyran-4-yl)methyl-7-chloro-1H-indole-3-carboxylic acid amide (8.0 g, 27.0 mmol) as a white solid. The remaining filtrate was washed with water (2×100 ml), dried over sodium sulfate, and concentrated in vacuo, to afford 1-(tetrahydropyran-4-yl)methyl-7-chloro-1H-indole-3-carboxylic acid amide (5.0 g, 17.0 mmol) as a brown solid.

Step D: 7-Chloro-3-([1,3,1]-oxathiazol-2-on-5-yl)-1-(tetrahydropyran-4-yl)methyl-1H-indole To a suspension of 1-(tetrahydropyran-4-yl)methyl-7-chloro-1H-indole-3-carboxylic acid amide (8.0 g, 27.0 mmol) in tetrahydrofuran (100 ml) was added chlorocarbonylsulfenyl chloride (4.7 ml, 55.0 mmol) and the reaction mixture was heated at reflux for 3 h and allowed to cool. The precipitate was filtered off and dried to give 5-(1-tetrahydropyran-4-yl) methyl-7-chloro-1H-indole)-[1,3,4]-oxathiazol-2-one (5.3 g, 15.0 mmol) as a white solid. The filtrate was concentrated in vacuo, and the resulting solid was washed with 5% ethylacetate in n-heptane then dried to leave 7-chloro-3-([1,3,4]-oxathiazol-2-on-5-yl)-1-(tetrahydropyran-4-yl)methyl-1H-indole (2.6 g, 7.0 mmol) as a pink solid.

Step E: 7-Chloro-3-({5-ethylcarboxylate}-([1,2,4]thiadiazol-3-yl))-1-(tetrahydropyran-4-yl)methyl-1H-indole To a suspension of 7-chloro-3-([1,3,4]-oxathiazol-2-on-5-yl)-1-(tetrahydropyran-4-yl)methyl-1H-indole (0.79 g, 2.0 mmol) in m-xylene (10 ml) was added ethylcyanoformate (2.2 ml, 23 mmol) and the reaction subjected to microwave irradiation at 180° C. for 15 mins using an Emrys Optimizer EXP™. The reaction was repeated ten times on the same scale, combined and solvent removed in vacuo to give 7-chloro-3-({5-ethylcarboxylate}-([1,2,4]thiadiazol-3-yl))-1-(tetrahydropyran-4-yl)methyl-1H-indole (7.1 g, 17 mmol) as a white solid.

Step F: 7-Chloro-3-({5-hydroxymethyl}-([1,2,4]thiadiazol-3-yl))-1-(tetrahydropyran-4-yl)methyl-1H-indole To a cooled solution (ice/methanol bath) of 7-chloro-3-({5-ethylcarboxylate}-([1,2,4]thiadiazol-3-yl))-1-(tetrahydropyran-4-yl)methyl-1H-indole (7.1 g, 17.0 mmol) in tetrahydrofuran (80 ml) and methanol (80 ml) was added sodium borohydride (1.9 g, 50.0 mmol) portionwise. The reaction was stirred for 18 h and then quenched with 1M hydrochloric acid (20 ml). The methanol and tetrahydrofuran were removed in vacuo and dichloromethane (200 ml) and 2M hydrochloric acid (50 ml) were added. The organics were separated and washed with brine (50 ml), dried over sodium sulfate and the solvent removed in vacuo. The resulting residue was purified by flash column chromatography eluting with 20%-50% (v/v) ethylactetate in n-heptane to give 7-chloro-3-({5-hydroxymethyl}-([1,2,4]thiadiazol-3-yl))-1-(tetrahydropyran-4-yl)methyl-1H-indole (3.6 g, 10.0 mmol) as a light pink solid.

Step G: Methanesulfonic acid 3-(1-{tetrahydropyran-4-yl}methyl-7-chloro-1H-indol-3-yl)-[1,2,4]thiadiazol-5-ylmethyl ester To a cooled solution (ice/methanol bath) of 7-chloro-3-({5-hydroxymethyl}-([1,2,4]thiadiazol-3-yl))-1-(tetrahydropyran-4-yl)methyl-1H-indole (3.6 g, 10.0 mmol) in dichloromethane (150 ml) was added methanesulfonyl chloride (0.97 ml, 12.0 mmol) and triethylamine (2.6 ml, 20.0 mmol) sequentially. The reaction was allowed to stir for 1 h and then poured into a separating funnel. The organics were washed with 5% aqueous sodium carbonate solution (2×100 ml), brine (1×100 ml), dried over sodium sulfate and the solvent removed in vacuo to afford methanesulfonic acid 3-(1-{tetrahydropyran-4-yl}methyl-7-chloro-1H-indol-3-yl)-[1,2,4]thiadiazol-5-ylmethyl ester (4.6 g, 10.0 mmol) which was used without further purification.

Step H: 7-Chloro-3-({5-[N-(morpholin-1-ylcarboxamido)methyl]aminomethyl}-([1,2,4]-thiadiazol-3-yl))-1-(tetrahydropyran-4-yl)methyl-1H-indole To a solution of methanesulfonic acid 3-(1-{tetrahydropyran-4-yl}methyl-7-chloro-1H-indol-3-yl)-[1,2,4]thiadiazol-5-ylmethyl ester (0.20 g, 0.45 mmol) in 1-methyl-2-pyrrolidinone (4 ml) was added 2-amino-(1-morpholin-4-yl) ethanone hydrochloride (0.98 g, 0.54 mmol) and potassium carbonate (0.90 g, 0.68 mmol). The reaction was stirred at room temperature for 18 h. The reaction was diluted with dichloromethane (8 ml) and filtered through a 5 g Strata™ SCX giga tube. The tube was washed with methanol and then eluted with 2 M ammonia in methanol. The methanolic ammonia solution was evaporated to afford the title compound (115 mg, 0.23 mmol) as the free base. The free base (0.04 g, 0.08 mmol) was dissolved in dichloromethane and hydrogen chloride (2M solution in diethyl ether; 1.0 ml, 2.0 mmol) was added. The mixture was concentrated in vacuo and recrystallised from 30% (v/v) dichloromethane in diethylether to afford the title compound, (0.02 g, 0.037 mmol), as a 1:1 hydrochloride salt. EsIMS: m/z 490.3 [M+H]$^+$.

EXAMPLE 2

(+/−)-7-Chloro-3-[(5-{2-carboxypyrrolidin-1-yl]methyl)-([1,2,4]-thiadiazol-3-yl)}-1-(tetrahydropyran-4-yl)methyl-1H-indole, hydrochloride salt Methanesulfonic acid 3-(1-{tetrahydropyran-4-yl}methyl-7-chloro-1H-indol-3-yl)-[1,2,4]thiadiazol-5-ylmethyl ester (Example 1; Step 1G; 0.08 g, 0.18 mmol) was dissolved in acetonitrile (2 ml). DL-proline (0.1 g, 0.9 mmol) was added and the mixture was subjected to microwave irradiation for 20 min at 150° C. The mixture was filtered and purified by semi-prep. HPLC (Method i) to afford the title compound, (0.005 g, 0.009 mmol), as a 1:1 trifluoroacetic acid salt. EsIMS: m/z 461.0 [M+H]$^+$.

EXAMPLE 3

7-Chloro-3-[(5-{4-spiro[(2-pyrrolidinone)-3-yl]piperidin-1-yl}methyl)-([1,2,4]-thiadiazol-3-yl)]-1-(tetrahydropyran-4-yl)methyl-1H-indole, hydrochloride salt Methanesulfonic acid 3-(1-{tetrahydropyran-4-yl}methyl-7-chloro-1H-indol-3-yl)-[1,2,4]thiadiazol-5-ylmethyl ester (Example 1; Step 1G; 0.10 g, 0.23 mmol) was dissolved in 1-methyl-2-pyrrolidinone (1 ml) and 4-spiro-[3-(2-pyrrolidinone)]piperidine hydrochloride (0.21 g, 1.1 mmol) and potassium carbonate (0.30 g, 2.3 mmol) was added and the mixture was subjected to microwave irradiation for 5 min at 100° C. The mixture was filtered through a 5 g Strata™ SCX giga tube. The tube was washed with methanol and then eluted with 2 M ammonia in methanol. Purified by semi-prep HPLC (Method ii) to afford the title compound, (0.03 g, 0.062 mmol), as the free base. EsIMS: m/z 500.0 [M+H]$^+$.

EXAMPLE 3A (S)-7-Chloro-3-[(5-{[({N-carboxamido}methyl)-2-carboxamide]pyrrolidin-1-yl}methyl)-([1,2,4]-thiadiazol-3-yl)]-1-(tetrahydropyran-4-yl)methyl-1H-indole, hydrochloride salt 7-Chloro-3-[(5-{[({N-carboxy}methyl)-2-carboxamide]pyrolidin-1-yl}methyl)-([1,2,4]-thiadiazol-3-yl)]-1-(tetrahydropyran-4-yl)methyl-1H-indole was prepared according to the method of Example 3 using H-Pro-Gly-OH instead of 4-spiro-[3-(2-pyrrolidinone)]piperidine hydrochloride. 7-Chloro-3-[(5-{[({N-carboxy}methyl)-2-carboxamide]pyrolidin-1-yl}methyl)-([1,2,4]-thiadiazol-3-yl)]-1-(tetrahydropyran-4-yl)methyl-1H-indole (35 mg, 0.068 mmol) was dissolved in dichloromethane, oxalyl chloride was added (0.012 ml, 0.14 mmol) and the reaction was stirred for 18 h at room temperature. Dichloromethane and excess oxalyl chloride were removed by evaporation and the obtained residue was mixed with dichloromethane (10 ml). Aqueous ammonia solution was added and reaction was stirred for 1 h. The mixture was transferred to a separating funnel and washed with water (2×10 ml), dried with sodium sulfate and concentrated in vacuo. Purified by semi-prep. HPLC (Method ii) to afford the title compound, (0.008 g, 0.015 mmol), as the free base. EsIMS: m/z 517.2 [M+H]$^+$, $[\alpha]_D^{22}$+1.7° (c=0.60 mg/ml in methanol).

EXAMPLE 4

(R)-7-Chloro-3-[(5-{[3-N-acetylamino]pyrrolidin-1-yl}methyl)-([1,2,4]-thiadiazol-3-yl)]-1-(tetrahydropyran-4-yl)methyl-1H-indole, hydrochloride salt Methanesulfonic acid 3-(1-{tetrahydropyran-4-yl}methyl-7-chloro-1H-indol-3-yl)-[1,2,4]thiadiazol-5-ylmethyl ester (Example 1; Step 1G; 100 mg, 0.227 mmol) was dissolved in dichloromethane (1 ml) and 3(R)-(+)-acetamidopyrrolidine (0.145 g, 1.14 mmol) was added and the mixture was subjected to microwave irradiation for 3 min at 100° C. The reaction was then diluted in dichloromethane and transferred to separating funnel, washed with sodium bicarbonate solution and the organic layer was dried with magnesium sulfate. The mixture was filtered through a 5 g Strata™ SCX giga tube. The tube was washed with methanol and then eluted with 2 M ammonia in methanol. The solvent was removed in vacuo to afford the title compound (70.1 mg, 0.148 mmol). EsIMS: m/z: 474.0 [M+H], $[\alpha]_D^{22}$+28.8° (c=2.60 mg/ml in methanol).

EXAMPLE 4A

7-Chloro-3-[(5-{2-(R)-[hydroxymethyl]pyrrolidin-1-yl}methyl)-([1,2,4]-thiadiazol-3-yl)]-1-(tetrahydropyran-4-yl)methyl-1H-indole, hydrochloride salt The title compound was prepared following the method of Example 4 and purified according to HPLC (Method ii), using L-(+)-prolinol instead of 3-acetamidopyrrolidine. EsIMS: m/z: 447.0 [M+H]

EXAMPLE 5

7-Methoxy-3-[(5-{[(N-carboxamido)methyl]methylamino}methyl)-([1,2,4]-thiadiazol-3-yl)]-1-(tetrahydropyran-4-yl) methyl-1H-indole, trifluoroacetic acid salt Methanesulfonic acid 3-(1-tetrahydropyran-4-yl)methyl-7-methoxy-indol-3-yl)-([1,2,4]thiadiazol-5-ylmethyl ester (106 mg, 0.25 mmol), prepared according to the method of Example 1 using 7-methoxyindole instead of 7-chloroindole, was dissolved in acetonitrile (2 ml) and transferred into a microwave vial. N-methyl glycine amide hydrochloride (53 mg, 1.26 mmol) and potassium carbonate (174 mg, 1.26 mmol) were added and the reaction mixture subjected to microwave irradiation at 150° C. for 30 mins using an Emrys Optimizer EXP™. The free base was purified by semi-prep. HPLC (Method i) to afford the title compound as a 1:1 trifluoroacetic acid salt (17.4 mg, 0.03 mmol). EsIMS: m/z 452.1 [M+Na]$^+$, 429.8 [M+H]$^+$

EXAMPLE 6

7-Chloro-3-[(5-{N-[2-methylsulfonamido]ethyleneamino}methyl)-([1,2,4]-thiadiazol-3-yl)]-1-(tetrahydropyran-4-yl)methyl-1H-indole, hydrochloride salt A mixture of methanesulfonic acid 3-[7-chloro-1-(tetrahydropyran-4-yl)methyl-1H-indol-3-yl]-([1,2,4]-thiadiazol-5-ylmethyl ester (Example 1; Step 1G; 44 mg, 0.10 mmol), potassium carbonate (55 mg, 0.4 mmol) and N-(methanesulfonamido)ethylenediamine hydrochloride salt (35 mg, 0.20 mmol) in tetrahydrofuran (2 ml)/acetonitrile (2 ml) was subjected to microwave irradiation at 160° C. for 10 mins. The reaction mixture was filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 67-100% (v/v) ethyl acetate in n-heptane, then 10% (v/v) methanol in ethyl acetate to give the free base of the title compound. Hydrochloride salt formation was achieved by the addition of hydrogen chloride (1M solution in diethyl ether; 1 ml) to a solution of the free base in diethyl ether (5 ml). The mixture was concentrated in vacuo to afford the title compound as a 1:1 hydrochloride salt (10 mg, 0.022 mmol). EsIMS: m/z 506.0 [M+Na]$^+$, 484.4 [M+H]$^+$.

EXAMPLE 6A

7-Chloro-3-[(5-{[(N-carboxamido)methyl]amino}methyl)-([1,2,4]-thiadiazol-3-yl)]-1-(tetrahydropyran-4-yl)methyl-1H-indole, hydrochloride salt The title compound was prepared following the method of Example 6, using glycinamide hydrochloride instead of N-(methanesulfonamido)ethylenediamine hydrochloride salt. EsIMS: m/z 442.1 [M+Na]$^+$, 420.0 [M+H]$^+$.

EXAMPLE 7

7-Chloro-3-({5-[(N-{2-methoxy}ethyl)-(N-{methylsulfonyl}amino]methyl}-([1,2,4]-thiadiazol-3-yl))-1-(tetrahydropyran-4-yl)methyl-1H-indole A mixture of methanesulfonic acid 3-[7-chloro-1-(tetrahydropyran-4-yl)methyl-1H-indol-3-yl]-([1,2,4]-thiadiazol-5-ylmethyl ester (Example 1; Step 1G; 60 mg, 0.14 mmol) and 2-methoxyethylamine (41 mg, 0.54 mmol) in tetrahydrofuran (2 ml) was subjected to microwave irradiation at 160° C. for 10 mins. The reaction mixture was filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 0-10% (v/v) methanol in ethyl acetate to give 7-chloro-3-[(5-{[N-(2-methoxyethyl)amino]methyl})-([1,2,4]-thiadiazol-3-yl)]-1-(tetrahydropyran-4-yl)methyl-1H-indole (58 mg, 0.14 mmol). A mixture of 7-chloro-3-[(5-{[N-(2-methoxyethyl)amino]methyl})-([1,2,4]-thiadiazol-3-yl)]-1-(tetrahydropyran-4-yl)methyl-1H-indole (58 mg, 0.14 mmol), triethylamine (17 mg, 0.17 mmol) and methanesulfonyl chloride (19 mg, 0.17 mmol) in dichloromethane (2 ml) was stirred at room temperature for 18 h. The excess amount of methanesulfonyl chloride was quenched with methanol (0.5 ml) and the mixture was purified by column chromatography eluting with 33-67% (v/v) ethyl acetate in n-heptane to give the title compound (37 mg, 0.074 mmol). EsIMS: m/z 521.0 [M+Na]$^+$, 499.1 [M+H]$^+$.

EXAMPLE 7A

7-Chloro-3-[(5-{[(N-{carboxamido}methyl)]-(N-{2-methoxyethylsulfonyl})amino}methyl)-([1,2,4]-thiadiazol-3-yl)]-1-tetrahydropyran-4-yl)methyl-1H-indole The title compound was prepared following the method of Example 7, using 7-chloro-3-[(5-{N-[(carboxamido)methyl]amino}methyl)-([1,2,4]-thiadiazol-3-yl)]-1-(tetrahydropyran-4-yl)methyl-1H-indole, (Example 6A) and 2-methoxyethanesulfonyl chloride instead of methanesulfonyl chloride. EsIMS: m/z 564.0 [M+Na]$^+$, 542.0 [M+H]$^+$.

EXAMPLE 8

7-Chloro-3-[(5-{N-[(2-sulfonamido)-2-methoxyethyl]ethyleneamino}methyl)-([1,2,4]-thiadiazol-3-yl)]-1-(tetrahydropyran-4-yl)methyl-1H-indole, hydrochloride salt To a solution of N-(2-tert-butoxycarbonyl)-ethylenediamine (0.63 ml, 4.00 mmol) and triethylamine (0.67 ml, 4.80 mmol) in dichloromethane (10 ml) was added 2-methoxyethanesulfonyl chloride (761 mg, 4.80 mmol) at 0° C., and the mixture was stirred at room temperature for 3 h. The reaction mixture was partitioned between dichloromethane and water. The aqueous layer was extracted with dichloromethane. The combined organic layers were washed with brine, dried over sodium sulfate, and concentrated in vacuo to obtain N-(2-tert-butoxycarbonylaminoethyl)-2-methoxyethanesulfonamide. The mixture of N-(2-tert-butoxycarbonylaminoethyl)-2-methoxyethanesulfonamide and 5N HCl (8 ml) in methanol (8 ml) was stirred at room temperature for 2 h, then at 50° C. for 1 h, and concentrated in vacuo to obtain N-(2-aminoethyl)-2-methoxyethanesulfonamide hydrochloride salt. The free base of the title compound was prepared following the method of Example 6 using methanesulfonic acid 3-[7-chloro-1-(tetrahydropyran-4-yl)methyl-1H-indol-3-yl]-([1,2,4]-thiadiazol-5-yl)methyl ester and N-(2-aminoethyl)-2-methoxyethanesulfonamide hydrochloride salt. The obtained crude free base of the title compound was purified by prep. LCMS to afford the trifluoroacetic acid salt of the title compound. EsIMS: m/z 528.0 [M+H]$^+$.

EXAMPLE 9

7-Ethyl-3-[(5-{[N-(carboxamido)methyl]-N-methylamino}methyl)-([1,2,4]-thiadiazol-3-yl)]-1-(tetrahydropyran-4-yl)methyl-1H-indole, hydrochloride acid salt Methanesulfonic acid 3-(1-tetrahydropyran-4-yl)methyl-7-ethyl-1H-indol-3-yl)-([1,2,4]thiadiazol-5-ylmethyl ester (30 mg, 0.07 mmol) prepared according to Example 1, using 7-ethylindole instead of 7-chloroindole, was dissolved in dry dichloromethane (1 ml) in a 5 ml microwave vial and potassium carbonate was added (70 mg, 0.51 mmol) followed by N-methyl glycine amide hydrochloride (26 mg, 0.21 mmol). The mixture is heated in a microwave oven at 100° C. for 3 mins. After cooling down to room temperature, the mixture was partitioned between water and dichloromethane. The organic phase was separated, washed with water, dried over magnesium sulfate and evaporated in vacuo. The crude oil was prepurified on a 2 g SCX column and on a 2 g Si-based Isolute column eluting with 50%-100% (v/v) ethyl acetate in n-heptane. The free base was converted into its hydrochloride salt by dissolving it in dry dichloromethane and adding a 2M solution of HCl in ether to afford the title compound: (7.9 mg, 0.017 mmol). EsIMS: m/z 428.1 [M+H]$^+$.

EXAMPLE 10

(+/−)-7-Ethyl-3-[(5-{[3-methylsulfonyl]pyrrolidin-1-yl}methyl)-([1,2,4]-thiadiazol-3-yl)]-1-(tetrahydropyran-4-yl)methyl-1H-indole, hydrochloride salt Methanesulfonic acid 3-(1-tetrahydropyran-4-yl)methyl-7-ethyl-1H-indol-3-yl)-([1,2,4]thiadiazol-5-ylmethyl ester (60 mg, 0.14 mmol) prepared according to Example 1 using 7-ethylindole instead of 7-chloroindole, was dissolved in dry dichloromethane (1 ml) in a 5 ml microwave vial followed by (+/−)-3-(methylsulfonyl)pyrrolidine (104 mg, 0.7 mmol). The mixture was heated in a microwave oven at 100° C. for 3 mins (fixed hold time switched on). After cooling down to room temperature, the mixture was diluted with dichloromethane, then washed with water and dried over magnesium sulfate. After evaporation to dryness, the crude product was purified a 2 g Si-based Isolute column eluting with 50%-100% (v/v) ethyl acetate in n-heptane. The fractions containing the product were combined, evaporated to dryness and further purified over a 2 g Strata™ SCX column. The free base is converted into its hydrochloride salt by dissolving it in dry dichloromethane and adding a 2M solution of HCl in ether, to afford the title compound: (8.0 mg, 0.015 mmol). EsIMS: m/z 489.1 [M+H]$^+$.

EXAMPLE 10A

7-Ethyl-3-[(5-{4-[(N-{2-hydroxy}ethyl)carboxamido]piperidin-1-yl}methyl)-(1,2,4]-thiadiazol-3-yl)-1-(tetrahydropyran-4-yl)methyl-1H-indole, The title compound was prepared according to Example 1, using methanesulfonic acid 3-(1-tetrahydropyran-4-yl)methyl-7-ethyl-1H-indol-3-yl)-([1,2,4]thiadiazol-5-ylmethyl ester instead of 3-(1-tetrahydropyran-4-yl)methyl-7-chloro-1H-indol-3-yl)-([1,2,4]thiadiazol-5-ylmethyl ester and 4-[({2-hydroxy}ethyl)-carboxamido]piperidine instead of 2-amino-1-morpholin-4-yl-ethanone hydrochloride. EsIMS: m/z 512.3 [M+H]$^+$.

EXAMPLE 11

(+/−)-7-Ethyl-3-[(5-{[2-hydroxymethyl]morpholin-4-yl}methyl)-([1,2,4]-thiadiazol-3-yl)]-1-(tetrahydropyran-4-yl)methyl-1H-indole Methanesulfonic acid 3-(1-tetrahydropyran-4-yl)methyl-7-ethyl-1H-indol-3-yl)-([1,2,4]thiadiazol-5-ylmethyl ester (60 mg, 0.14 mmol) is dissolved in dry acetonitrile (1.5 ml) in a 5 ml microwave vial followed by (+/−)-2-hydroxymethyl-morpholine trifluoroacetic acid salt (207 mg, 0.9 mmol), potassium carbonate (200 mg, 1.47 mmol) and potassium iodide (150 mg; 0.9 mmol). The mixture is heated in a microwave oven at 160° C. for 5 mins. After cooling down to room temperature, the mixture is evaporated to dryness and the residue partitioned between dichloromethane and water. The aqueous phase is separated, washed again with water, and the organic phase is then dried over magnesium sulfate and evaporated to dryness. The crude product is purified a 2 g Si-based Isolute column eluting with 50%-100% (v/v) ethyl acetate in n-heptane. The fractions containing the product are combined, evaporated to dryness and further purified over a 2 g SCX column. The free base is converted into its hydrochloride salt by dissolving it in dry dichloromethane and adding a 2M solution of HCl in ether, to afford the title compound: (44.3 mg, 0.09 mmol). EsIMS: m/z 457.4 [M+H]$^+$.

The method of Example 5 was further used to prepare the following compounds using alternative amines instead of N-methyl glycine amide hydrochloride, a reaction time of 5 mins instead of 30 mins, and purification according to method Example 10.

EXAMPLE 12

7-Ethyl-3-[(5-{N-[4-(carboxamido)methyl]piperidin-1-yl}methyl)-([1,2,4]-thiadiazol-3-yl)]-1-(tetrahydropyran-4-yl)methyl-1H-indole The title compound was prepared using piperidine-4-N-methyl carboxylic acid amide. EsIMS: m/z 482.1 [M+H]$^+$.

EXAMPLE 12A

7-Ethyl-3-[(5-{[(S)-(methylcarboxylate)methyl]-N-(1-hydroxymethyl)methylamino}-methyl)-([1,2,4]-thiadiazol-3-yl)]-1-(tetrahydropyran-4-yl)methyl-1H-indole The title compound was prepared using (S)—N-methyl-serine. EsIMS: m/z 473.0 [M+H]$^+$.

EXAMPLE 12B

7-Ethyl-3-[(5-{[N-(2,3-dihydroxypropyl)] methylamino}methyl)-([1,2,4]-thiadiazol-3-yl)]-1-(tetrahydropyran-4-yl)methyl-1H-indole The title compound was prepared using N-methyl-N-(2,3-dihydroxypropyl)amine EsIMS: m/z 445.4 [M+H]$^+$.

EXAMPLE 13

(S)-7-Chloro-3-[(5-{[3-N-(2-hydroxyethyl)carboxamido]piperidin-1-yl}methyl)-([1,2,4]-thiadiazol-3-yl)]-1-(1,1-dioxo-hexahydrothiopyran-4-yl)methyl-1H-indole, hydrochloride salt Step A: 7-Chloro-1-[(1,1-dioxohexahydrothiopyran-4-yl)methyl]-1H-indole A solution of 7-chloroindole (45 g, 296 mmol) in dimethylformamide (450 ml) was treated portionwise with sodium hydride (60% dispersion in mineral oil; 17.8 g, 444 mmol). The mixture was stirred at room temperature for 30 minutes. Toluene-4-sulfonic acid 1,1-dioxo-hexahydro-1-thiopyran-4-ylmethyl ester (95.45 g, 300 mmol) was then added portionwise over 15 minutes and the mixture stirred at room temperature for 72 h. The reaction was quenched with water (2 L) and the precipitate filtered off, washing with water (3×300 ml) and dried to afford the title compound as a colourless solid (79 g, 266 mmol).

Step B: 7-Chloro-1-[(1,1-dioxo-hexahydrothiopyran-4-yl)methyl]-1H-indole-3-carboxylic acid A solution of 1-[(1,1-dioxohexahydrothiopyran-4yl)methyl]-7-chloro-1H-indole (79 g, 266 mmol) in dimethylformamide (800 ml) was cooled in an acetone/ice bath under nitrogen and trifluoroacetic anhydride (74.3 ml, 532 mmol) was added dropwise, maintaining the temperature below 5° C. The mixture was allowed to warm to room temperature with stirring over 2 h, and then quenched with water (3 L). The resulting 7-chloro-1-[(1,1-dioxo-hexahydrothiopyran-4-yl)methyl]-3-[(trifluoromethyl)-carbonyl]-1H-indole precipitate was filtered off, washing with water (3×700 ml). The damp solid was suspended in ethanol (500 ml), 4 M aqueous sodium hydroxide (500 ml) was added and the mixture was heated to reflux with stirring for 2 h. The mixture was cooled and the ethanol removed in vacuo. Water (500 ml) and n-heptane (200 ml) were added and the mixture acidified to pH 2 with 5M aqueous hydrochloric acid. The suspension was filtered off, washing with water (3×500 ml) and dried to afford the title compound as a light brown solid (70 g, 205 mmol).

Step C: 7-Chloro-1-[(1,1-dioxo-hexahydrothiopyran-4-yl)methyl]-1H-indole-3-carboxamide A solution of 7-chloro-1-[(1,1-dioxo-hexahydrothiopyran-4yl)methyl]-1H-indole-3-carboxylic acid (70 g, 205 mmol) in tetrahydrofuran (750 ml) was cooled to 0° C. under nitrogen and oxalyl chloride (23 ml, 266 mmol) was added dropwise. The mixture was stirred at room temperature for 16 h, the volatile components evaporated in vacuo and the residue suspended in dichloromethane. The resulting mixture was added slowly (over 3 minutes) to a cooled (0° C.) mixture of ammonium hydroxide (33% solution in water, 750 ml) and potassium carbonate (56.5 g, 410 mmol). The resulting biphasic suspension was stirred for 1 h. The dichloromethane was then removed in vacuo and the pH adjusted to 8-9 with aqueous hydrochloric acid. The suspension was then filtered off, washing with water (2×300 ml), n-heptane (2×300 ml) and diethyl ether (2×300 ml) and dried to afford the title compound as a sandy coloured solid (66.5 g, 195 mmol).

Step D: 7-Chloro-1-[(1,1-dioxo-hexahydrothiopyran-4-yl)methyl]-3-([1,3,4]-oxathiazol-2-on-5-yl)-1H-indole A mixture of 7-chloro-1-[(1,1-dioxo-hexahydrothiopyran-4-yl)methyl]-1H-indole-3-carboxamide (10.0 g, 29.3 mmol) and chlorocarbonylsulfenylchloride (5.05 ml, 60.9 mmol) in tetrahydrofuran (150 ml) was refluxed gently under nitrogen with stirring for 3 h. The reaction mixture was concentrated in vacuo, cooled and the solid filtered off. The solid was taken up in acetone and the mixture was concentrated in vacuo, cooled and the resulting buff coloured solid filtered off and dried to afford the title compound (8.7 g, 21.8 mmol).

Step E: 7-Chloro-1-[(1,1-dioxo-hexahydrothiopyran-4-yl)methyl]-3-[(5-ethoxycarbonyl)-([1,2,4]thiadiazol-3-yl)]-1H-indole: approx. 1:1 mixture with 7-chloro-3-cyano-1-[(1,1-dioxo-hexahydrothiopyran-4-yl)methyl]-1H-indole A mixture of 7-chloro-1-[(1,1-dioxo-hexahydrothiopyran-4-yl)methyl]-3-([1,3,4]-oxathiazol-2-on-5-yl)-1H-indole (8.3 g, 20.8 mmol) and ethylcyanoformate (20 ml, 202 mmol) in mixed xylenes (200 ml) was heated at vigorous reflux for 3 h. The resulting solution was concentrated in vacuo, cooled and diluted with n-heptane until no further precipitation occurred. The resulting solid was filtered off, washing with n-heptane and dried to afford the title mixture as a buff coloured solid (8.2 g)

Step F: 7-Chloro-1-[(1,1-dioxo-hexahydrothiopyran-4-yl)methyl]-3-[(5-hydroxymethyl)-([1,2,4]thiadiazol-3-yl)]-1H-indole To a solution of the above mixture of 7-chloro-1-[(1,1-dioxo-hexahydrothiopyran-4-yl)methyl]-3-[(5-ethylcarboxyl)-([1,2,4]thiadiazol-3-yl)]-1H-indole and 7-chloro-3-cyano-1-[(1,1-dioxo-hexahydrothiopyran-4-yl)methyl]-1H-indole (8.0 g) in dichloromethane/methanol (1:1; 240 ml) at room temperature was added sodium borohydride (1.34 g, 35.4 mmol) portionwise over 5 minutes. The reaction was stirred for 15 minutes. Acetone (20 ml) was then added and the mixture stirred for a further 5 minutes. The mixture was concentrated in vacuo to low volume and diluted with water until no further precipitation occurred. The precipitate was filtered off, washing with water and air dried. The solid was dissolved in dichloromethane (200 ml), washed with water (100 ml), brine (100 ml), dried over sodium sulfate and filtered. The solution was concentrated in vacuo. The title compound crystallised out on standing and was filtered off (4.5 g, 10.9 mmol). Further concentration of the filtrate resulted in crystallisation of the nitrile that was carried through from the previous step, 7-chloro-3-cyano-1-[(1,1-dioxo-hexahydrothiopyran-4-yl)methyl]-1H-indole (1.7 g).

Step G: 7-Chloro-1-[(1,1-dioxo-hexahydrothiopyran-4-yl)methyl]-3-{5-[(methanesulfonyloxy)methyl]-([1,2,4]-thiadiazol-3-yl)}-1H-indole To a suspension of 7-chloro-1-[(1,1-dioxo-hexahydrothiopyran-4-yl)methyl]-3-[(5-hydroxymethyl)-([1,2,4]thiadiazol-3-yl)]-1H-indole (4.5 g, 10.9 mmol) in dichloromethane (200 ml) was added N,N-diisopropylethylamine (3.7 ml, 21.4 mmol) followed by methanesulfonyl chloride (1.01 ml, 13.1 mmol) dropwise over 2-3 minutes. The reaction was stirred for 15 minutes, then quenched with ice cold water and stirred for a further 10 minutes. The layers were separated and the organic phase washed with water (100 ml), brine (100 ml), dried over sodium sulfate and filtered. The solvent was removed in vacuo and the residue re-crystallised from acetone to afford the title compound as a pink solid (4.2 g, 8.6 mmol).

Step H: (S)-7-Chloro-3-[(5-{[3-N-(2-hydroxyethyl)carboxamido]piperidin-1-yl}methyl)-([1,2,4]-thiadiazol-3-yl)]-1-(1,1-dioxo-hexahydrothiopyran-4-yl)methyl-1H-indole, hydrochloride salt A mixture of 7-chloro-1-[(1,1-dioxo-hexahydrothiopyran-4-yl)methyl]-3-{5-[(methanesulfonyloxy)methyl]-([1,2,4]-thiadiazol-3-yl)}-1H-indole (245 mg, 0.5 mmol), (S)—N-(2-hydroxyethyl)nipecotamide (103 mg, 0.6 mmol) [prepared from standard amide coupling of commercial (S)Boc-nipecotic acid and ethanolamine] and potassium carbonate (103 mg, 0.75 mmol) in acetone (10 ml) was heated at reflux for 5 h. As the reaction was incomplete, additional (S)—N-(2-hydroxyethyl)nipecotamide (40 mg) was added and reflux continued for a further 2 h. After filtering off inorganics, solvent was removed in vacuo and the residue partitioned between dichloromethane and water. The crude product was then filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 4-6% (v/v) ethanol in dichloromethane to give the free base of the title compound. Addition of hydrogen chloride (1M solution in diethyl ether) to a solution of the free base in dichloromethane (5 ml) followed by precipitation twice from dichloromethane plus trace methanol with ether afforded the title compound as a non-crystalline solid, 225 mg (0.37 mmol). EsIMS: m/z 566.5 [M+H]$^+$. $[\alpha]^D$ –3.37° (c=1.78 mg/mL in methanol).

EXAMPLE 13A

7-Chloro-3-[(5-{[4-(N-methyl)carboxamido]piperidin-1-yl}methyl)-([1,2,4]-thiadiazol-3-yl)]-1-(1,1-dioxo-hexahydro-thiopyran-4-yl)methyl-1H-indole, hydrochloride salt The title compound was prepared according to the method of Example 13 using piperidine-4-N-methyl carboxylic acid amide instead of (S)—N-(2-hydroxyethyl)nipecotamide in Step H, a reaction time of 2 h, and purification by watering out followed by cystallisation from acetone. EsIMS: m/z 536.5, 538.5 [M+H]+

EXAMPLE 14

7-Chloro-3-[(5-{[4-hydroxy]piperidin-1-yl}methyl)-([1,2,4]-thiadiazol-3-yl)]-1-(1,1-dioxo-hexahydro-thiopyran-4-yl)methyl-1H-indole, hydrochloride salt 7-Chloro-1-(1,1-dioxo-hexahydro-thiopyran-4ylmethyl)-3{-[5-[(methane-sulfonyloxy)methyl]-([1,2,4]-thiadiazol-3-yl)-1H-indole (98 mg, 0.2 mmol) was dissolved in 1-methyl-2-pyrrolidinone (0.5 ml), di-iso-propylethyl amine (69 µl, 0.4 mmol) and 4-hydroxy-piperidine (26 mg, 0.26 mmol) added and the mixture warmed to 40° C. for 3 h. The solution was cooled to room temperature and water slowly added to precipitate the product as a filterable semi-solid. The crude product chromatographed on silica, eluting with ethanol in dichloromethane 4% (v/v). Conversion to the hydrochloride salt was followed by precipitation from dichloromethane containing a trace of ethanol with diethyl ether to give the title compound as a non-crystalline solid, (55 mg, 0.11 mmol). EsIMS: m/z 495.4, 497.4 [M+H]+

EXAMPLE 14A

7-Chloro-3-[(5-{[N-(2-methoxy)ethyl] methylamino}methyl)-([1,2,4]-thiadiazol-3-yl)]-1-(1, 1-dioxo-hexahydro-thiopyran-4-yl)methyl-1H-indole, hydrochloride salt The title compound was prepared using N-2-(methoxyethyl)methylamine instead of 4-hydroxy-piperidine. EsIMS: m/z 483.3, 485.3 [M+H]+

EXAMPLE 14B

7-Chloro-3-[(5-{[N-(2-hydroxy)ethyl]methylamino] methyl)-([1,2,4]-thiadiazol-3-yl)]-1-(1,1-dioxo-hexahydro-thiopyran-4-yl)methyl-1H-indole, hydrochloride salt The title compound was prepared using 2-methylaminoethanol instead of 4-hydroxy-piperidine. EsIMS: m/z 469.5, 471.5 [M+H]+

EXAMPLE 14C

7-Ethyl-3-[(5-{[4-(methylsulfonamido)methyl]piperidin-1-yl}methyl)-([1,2,4]-thiadiazol-3-yl)-1-(tetrahydropyran-4-yl)methyl-1H-indole, hydrochloride salt The title compound was prepared using methanesulfonic acid 3-(1-tetrahydropyran-4-yl)methyl-7-ethyl-1H-indol-3-yl)-([1,2,4]thiadiazol-5-ylmethyl ester according to Example 1, using 7-ethylindole instead of 7-chloroindole, and according to Example 14 using N-(2-tert-butoxycarbonyl)-4-aminomethyl-piperidine instead of 4-hydroxy-piperidine. Removal of the N-(2-tert-butoxycarbonyl)-group was achieved using trifluoroacetic acid (2 ml) in dichloromethane (10 ml) at room temperature. Subsequent treatment of the trifluoroacetic acid salt with methanesulfonyl chloride (13.8 µl, 0.18 mmol) in dichloromethane and DIPEA (56 µl, 0.3 mmol) at room temperature gave the title compound following chromatography on silica. EsIMS: m/z 532.0 [M+H]+

EXAMPLE 15

7-Chloro-3-({5-[(N-{2-hydroxy}ethyl)-(N-{methylsulfonyl})amino]methyl}-([1,2,4]-thiadiazol-3-yl))-1-(tetrahydropyran-4-yl)methyl-1H-indole A mixture of methanesulfonic acid 3-[7-chloro-1-(tetrahydropyran-4-yl)methyl-1H-indol-3-yl]-[1,2,4]-thiadiazol-5-ylmethyl ester (Example 1; Step 1G; 300 mg, 0.68 mmol), glycine ethyl ester hydrochloride salt (114 mg, 0.82 mmol) and triethylamine (206 mg, 2.04 mmol) in tetrahydrofuran (4 ml) was subjected to microwave irradiation at 160° C. for 10 minutes. The reaction mixture was filtered through a 5 g Strata™ SCX giga tube. The tube was washed with methanol and then eluted with 2 M ammonia in methanol. The methanolic ammonia solution was concentrated in vacuo to give 7-chloro-3-[(5-{[(ethylcarboxylate)methyl]amino}methyl)-([1,2,4]-thiadiazol-3-yl)]-1-(tetrahydropyran-4-yl)methyl-1H-indole (144 mg, 0.32 mmol). A mixture of 7-chloro-3-[(5-{[(ethylcarboxylate)methyl]amino}methyl)-([1,2,4]-thiadiazol-3-yl)]-1-(tetrahydropyran-4-yl)methyl-1H-indole (60 mg, 0.13 mmol), triethylamine (19 mg, 0.19 mmol) and methanesulfonyl chloride (18 mg, 0.16 mmol) in dichloromethane (2 ml) was stirred at room temperature for 2 h. The excess amount of methanesulfonyl chloride was quenched with ethanol (0.5 ml) and the mixture was purified by column chromatography eluting with 33-60% (v/v) ethyl acetate in n-heptane to give 7-chloro-3-[(5-[({ethylcarboxylate}methyl)-(N-{methylsulfonyl})amino] methyl)-([1,2,4]-thiadiazol-3-yl)]-1-(tetrahydropyran-4-yl) methyl-1H-indole (46 mg, 0.87 mmol). To a solution of 7-chloro-3-[(5-[({ethylcarboxylate}methyl)-(N-{methylsulfonyl})amino]methyl)-([1,2,4]-thiadiazol-3-yl)]-1-(tetrahydropyran-4-yl)methyl-1H-indole (35 mg, 0.066 mmol) in the mixture of tetrahydrofuran (1 ml) and methanol (1 ml) was added sodium borohydride (10 mg, 0.27 mmol), and the mixture was stirred at room temperature for 18 h. The reaction mixture was quenched with 5N HCl (0.1 ml) and concentrated in vacuo. The residue was purified by column chromatography eluting with 33-100% (v/v) ethyl acetate in n-heptane, then 10% (v/v) methanol in ethyl acetate to give the title compound (19 mg, 0.039 mmol). EsIMS: m/z 507.0 [M+Na]+, 485.1 [M+H]+.

EXAMPLE 16

7-Chloro-1-(cyclohexyl)methyl-3-({4-[4-(hydroxymethyl)piperidin-1-yl]methyl}-[1,3]-thiazol-2-yl)-1H-indole, hydrochloride salt Step A: 7-Chloro-1-cyclohexylmethylindole To a solution of 7-chloroindole (4.91 g, 32.4 mmol) in dimethylformamide (60 ml) at 0° C. under nitrogen was added sodium hydride (60% dispersion in mineral oil, 1.43 g, 35.6 mmol). The mixture was stirred for 1 h at room temperature. Cyclohexylmethyl bromide (5.0 ml, 35.6 mmol) was added at 0° C. The mixture was stirred for 18 h at room temperature. To the reaction mixture was added sodium hydride (60% dispersion in mineral oil, 358 mg, 8.94 mmol). After stirring for 15 mins, cyclohexylmethyl bromide (1.25 ml, 8.96 mmol) was added. The mixture was heated at 70° C. with stirring for 1.5 h. After cooling to room temperature, the mixture was partitioned between dichloromethane and water. The aqueous layer was extracted with dichloromethane and combined organic layers were washed with brine, dried over sodium sulfate and concentrated in vacuo. The obtained residue was purified by column chromatography eluting with 0-5% (v/v) ethyl acetate in n-heptane to afford 7-chloro-1-cyclohexylmethylindole (8.1 g, 32.0 mmol).

Step B: 7-Chloro-1-(cyclohexyl)methyl-3-[(trifluoromethyl)carbonyl]-1H-indole A solution of 7-chloro-1-cyclohexylmethylindole (8.1 g, 32.0 mmol) in dimethylformamide (40 ml) was cooled to 0° C. under nitrogen and trifluoroacetic anhydride (4.1 ml, 36.0 mmol) was added. The mixture was stirred at room temperature for 4 h. The mixture was partitioned between ethyl acetate and water. The aqueous layer was extracted with ethyl acetate and combined organic layers were washed with brine, dried over sodium sulfate and concentrated in vacuo. The obtained crystals were washed with n-heptane to afford 7-chloro-1-(cyclo-hexyl)methyl-3-[(trifluoromethyl)carbonyl]-1H-indole (8.6 g, 25.0 mmol).

Step C: 7-Chloro-1-(cyclohexyl)methyl-1H-indole-3-carboxylic acid

The mixture of 7-chloro-1-(cyclohexyl)methyl-3-[(trifluoromethyl)carbonyl]-1H-indole (8.6 g, 25.0 mmol) and 4N NaOH (60 ml) in ethanol (40 ml) was stirred at 85° C. for 18 h. The mixture was concentrated in vacuo and the residue was acidified with 5N HCl, then partitioned between dichloromethane and water. The aqueous layer was extracted with dichloromethane and combined organic layers were washed with brine, dried over sodium sulfate and concentrated in vacuo. The obtained crystals were washed with n-heptane to afford 7-chloro-1-(cyclohexyl)methyl-1H-indole-3-carboxylic acid (6.4 g, 21.9 mmol).

Step D: 7-Chloro-1-(cyclohexyl)methyl-1H-indole-3-carboxylic acid amide

Oxalyl chloride (4.95 g, 39.0 mmol) was added dropwise to a mixture of 7-chloro-1-(cyclohexyl)methyl-1H-indole-3-carboxylic acid (6.4 g, 21.9 mmol) and dichloromethane (150 ml) under ice-water cooling and the resulting mixture was stirred at room temperate for 20 h. Dichloromethane and excess oxalyl chloride were removed by evaporation and the obtained residue was mixed with dichloromethane (100 ml). Aqueous ammonia (33%, 50 ml) and potassium carbonate (6.05 g, 43.8 mmol) was added into the mixture under ice-water bath cooling. After stirring at room temperature for 2 h, the reaction mixture was concentrated in vacuo, then the obtained solid was washed with water, then n-heptane, and dried under reduced pressure to afford 7-chloro-1-(cyclohexyl)methyl-1H-indole-3-carboxylic acid amide (6.4 g, 22.0 mmol).

Step E: 7-Chloro-3-[4-(chloromethyl)thiazol-2-yl]-1-(cyclohexyl)methyl-1H-indole A mixture of 7-chloro-1-(cyclohexyl)methyl-1H-indole-3-carboxylic acid amide (1.74 g, 6.0 mmol), Lawesson's reagent (4.85 g, 12.0 mmol), toluene (150 ml) and tetrahydrofuran (50 ml) was stirred at room temperature for 3 days. The reaction mixture was concentrated in vacuo and the obtained reside was purified by column chromatography eluting with 20-50% (v/v) ethyl acetate in n-heptane to afford 7-chloro-1-(cyclohexyl)methyl-1H-indole-3-carbothioic acid amide (1.38 g, 4.50 mmol). A mixture of 7-chloro-1-(cyclohexyl)methyl-1H-indole-3-carbothioic acid amide (921 mg, 3.00 mmol), 1,3-dichloroacetone (571 mg, 4.50 mmol) in toluene (30 ml) was stirred at 40° C. for 18 h. The reaction mixture was concentrated in vacuo, and the obtained crystals were washed with 10% dichloromethane (v/v) in n-heptane to give 7-chloro-3-[4-(chloromethyl)thiazol-2-yl]-1-(cyclohexyl)methyl-1H-indole (587 mg, 1.55 mmol).

Step F: 7-Chloro-1-(cyclohexyl)methyl-3-({4-[4-(hydroxymethyl)piperidin-1-yl]methyl}-[1,3]-thiazol-2-yl)-1H-indole A mixture of 7-chloro-3-[4-(chloromethyl)thiazol-2-yl]-1-(cyclohexyl)methyl-1H-indole (140 mg, 0.37 mmol), 4-(hydroxymethyl)piperidine (85 mg, 0.74 mmol), potassium carbonate (56 mg, 0.41 mmol), sodium iodide (55 mg, 0.37 mmol) and acetonitrile (3 ml) was subjected to microwave irradiation for 5 min at 160° C. The reaction mixture was filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 0-25% (v/v) methanol in ethyl acetate to give the free base of the title compound. Hydrochloride salt formation was achieved by the addition of hydrogen chloride (1M solution in diethyl ether; 2 ml) to a solution of the free base in diethyl ether (10 ml). The mixture was concentrated in vacuo to afford the title compound as a 1:1 hydrochloride salt (167 mg, 0.36 mmol). EsIMS: m/z 458.4 $[M+H]^+$.

EXAMPLE 16A

7-Chloro-1-(tetrahydropyran-4-yl)methyl-3-(4-{[N-(carboxamido)methyl-N-methylamino]methyl}-[1,3]-thiazol-2-yl)-1H-indole A mixture of 7-chloro-3-[4-(chloromethyl)thiazol-2-yl]-1-(tetrahydropyran-4-yl)methyl-1H-indole (prepared as described in Example 16, using toluene-4-sulfonic acid tetrahydropyran-4-ylmethyl ester instead of cyclohexylmethyl bromide) (40 mg, 0.10 mmol), N-methyl glycine amide hydrochloride (18.4 mg, 0.15 mmol), di-isopropylethylamine (35 µl, 0.21 mmol) and sodium iodide (16 mg, 0.10 mmol) in dimethylformamide (2 ml) was subjected to microwave irradiation for 5 min at 160° C. The reaction mixture was filtered through a 5 g Strata™ SCX giga tube. The tube was washed with dichloromethane and then eluted with 10% (2 M ammonia in methanol) in dichloromethane. The product was purified by column chromatography eluting with 3:97 (v/v) (2M ammonia in methanol): dichloromethane to give the title compound (39 mg, 0.09 mmol). EsIMS: m/z 433.5, 435.4 $[M+H]^+$.

EXAMPLE 17

7-Chloro-3-[(5-{4-[hydroxymethyl]piperidin-1-yl}methyl)-([1,3,4]-oxadiazol-2-yl)]-1-(cyclohexyl)methyl-1H-indole, hydrochloride salt To a suspension of 1-cyclohexylmethyl-7-chloro-1H-indole-3-carboxylic acid (as prepared in Example 16; (2.0 g, 6.8 mmol) in dichloromethane (60 ml) was added oxalyl chloride (1.2 ml, 14 mmol) and the reaction stirred for 2 h and left to stand overnight. The solvent and excess reagent was removed in vacuo. The resulting residue was dissolved in dichloromethane (10 ml) and added dropwise to a cooled solution (ice/methanol bath) of hydrazine hydrate (1.7 ml, 34 mmol) in diethyl ether (60 ml) over 5 mins. The reaction mixture was then stirred for a further 40 mins before being reduced to half its volume in vacuo and filtered. The filtrate was concentrated further and the resulting precipitate filtered. The precipitates were combined and dried in vacuo to afford 1-cyclohexylmethyl-7-chloro-1H-indole-3-carboxylic acid hydrazide (2.3 g, 7 mmol).

To a suspension of 1-cyclohexylmethyl-7-chloro-1H-indole-3-carboxylic acid hydrazide (0.71 g, 2.3 mmol) in dichloromethane (20 ml) was added potassium carbonate (1.6 g, 11 mmol) and the reaction stirred for 1 h. The reaction mixture was cooled in a dry ice/ethanol bath and chloroacetyl chloride (0.2 ml, 3.0 mmol) was added and the reaction stirred for 1 h. Saturated sodium bicarbonate solution (30 ml) was added and the reaction allowed to warm to room temperature. The reaction mixture was extracted with 9:1 (v/v) dichloromethane:methanol (3×20 ml), the organic phases combined, washed with brine (1×30 ml), dried over sodium sulfate, and solvent removed in vacuo to give 1-cyclohexylmethyl-7-chloro-1H-indole-3-carboxylic acid N-(2-chloroacetyl)hydrazide (0.6 g, 2.0 mmol).

To a solution of 1-cyclohexylmethyl-7-chloro-1H-indole-3-carboxylic acid N'-(2-chloroacetyl)hydrazide (0.6 g, 2.0 mmol) in tetrahydrofuran (5 ml) was added (methoxycarbonylsulfamoyl)triethylammonium hydroxide, inner salt (0.78 g, 3.0 mmol) and the resulting reaction mixture subjected to microwave irradiation at 150° C. for 15 mins. The reaction mixture was quenched with methanol and the solvent evaporated. The resulting residue was purified by flash chromatography using 33-50% (v/v) ethyl acetate in n-heptane to give 7-chloro-3-[(5-chloromethyl)-([1,3,4]-oxadiazol-2-yl]-1-(cyclohexyl)methyl-1H-indole (0.48 g, 1.0 mmol) as a yellow solid.

To a solution of 7-chloro-3-[(5-chloromethyl)-([1,3,4]-oxadiazol-2-yl]-1-(cyclohexyl)methyl-1H-indole (0.08 g, 0.2 mmol) in dichloromethane (2 ml) was added 4-piperidine methanol (0.13 g, 1.0 mmol) and the reaction mixture subjected to microwave irradiation at 100° C. for 20 mins. The resulting mixture was purified by semi-prep. HPLC (Method ii) to afford the title compound (10 mg, 0.02 mmol) as the free base. The free base was dissolved in dichloromethane and hydrogen chloride (2M solution in diethyl ether; 1.0 ml, 2.0 mmol) was added. The excess reagent and solvent were removed by evaporation to the leave the title compound (1:1 hydrochloride salt) as a white solid. EsIMS: m/z 443.3 [M+H]$^+$

EXAMPLE 18

(S)-7-Chloro-3-[(5-{N-methylsulfonyl}pyrrolidin-2-yl)-([1,3,4]-oxadiazol-2-yl)]-1-(tetrahydropyran-4-yl)methyl-1H-indole Step A: (S)-7-Chloro-3-[(5-{N-tert-butoxycarbonyl}pyrrolidin-2-yl)-([1,2]-dihydrazide)]-1-(tetrahydropyran-4-yl)methyl-1H-indole A mixture of 1-(tetrahydropyran)methyl-7-chloro-3-(carboxylic acid hydrazide)-1H-indole (prepared according to Example 17 using toluene-4-sulfonic acid tetrahydropyran-4-ylmethyl ester instead of cyclohexyl methyl bromide) (1.0 g, 3.2 mmol), O-benzotriazol-1-yl-N,N,N',N'-tetramethyluronium hexafluoro-phosphate (1.8 g, 4.7 mmol), di-iso-propylethylamine (1.6 ml, 9.1 mmol) and N-Boc-[L]-Proline (756 mg, 3.52 mmol) in dichloromethane (35 ml) was stirred at room temperature for 16 h. The reaction mixture was then washed with aqueous HCl and then saturated bicarbonate solution and the dichloromethane concentrated in vacuo. This afforded (S)-7-chloro-3-[(5-{N-tert-butoxycarbonyl}pyrrolidin-2-yl)-([1,2]-dihydrazide)]-1-(tetrahydropyran-4-yl)methyl-1H-indole (2.5 g, 50.0 mmol) as a brown gum.

Step B: (S)-7-Chloro-3-[(5-{N-tert-butoxycarbonyl}pyrrolidin-2-yl)-([1,3,4]-oxadiazol-2-yl)]-1-(tetrahydropyran-4-yl)methyl-1H-indole A mixture of (S)-7-chloro-3-[(5-{N-tert-butoxycarbonyl}pyrrolidin-2-yl)-([1,2]-dihydrazide)]-1-(tetrahydropyran-4-yl)methyl-1H-indole (2.5 g, 5 mmol), and Burgess reagent (1.43 g, 10 mmol), in tetrahydrofuran (15 ml) was subjected to microwave irradiation at 200° C. for 5 min using an Emrys Optimizer EXP™ in five batches. The reaction mixtures were concentrated in vacuo and the obtained residue was purified directly by flash column chromatography eluting with n-heptane then changing to diethyl ether and finally dichloromethane to afford (S)-7-chloro-3-[(5-{N-tert-butoxycarbonyl}pyrrolidin-2-yl)-([1,3,4]-oxadiazol-2-yl)]-1-(tetrahydropyran-4-yl)methyl-1H-indole (1.0 g, 2.0 mmol).

Step C: (S)-7-Chloro-3-[(5-{N-methylsulfonyl}pyrrolidin-2-yl)-([1,3,4]-oxadiazol-2-yl]-1-(tetrahydropyran-4-yl)methyl-1H-indole A mixture of (S)-7-chloro-3-[(5-{N-tert-butoxycarbonyl}pyrrolidin-2-yl)-([1,3,4]-oxadiazol-2-yl)]-1-(tetrahydropyran-4-yl)methyl-1H-indole (210 mg, 0.43 mmol), and trifluoroacetic acid (1 ml, 13.0 mmol), in dichloromethane (10 ml) was stirred at room temperature for 30 mins. The reaction mixture was concentrated in vacuo and the obtained residue was added to a mixture of triethylamine (93 µl, 0.66 mmol), methanesulfonyl chloride (21 µl, 0.3 mmol) and dimethylaminopyridine (2 mg, 0.018 mmol), in dichloromethane (10 ml) and left to stir at room temperature for 16 h. The organics were washed with 2M aqueous HCl solution (20 ml), dried over magnesium sulfate, filtered, and the solvent removed in vacuo. The obtained residue was purified directly by flash column chromatography eluting with dichloromethane and finally recrystallised with ethanol and water to afford the title compound (25 mg, 0.048 mmol) as a solid. EsIMS: 465.0 m/z [M+H]$^+$

EXAMPLE 18A (S)-7-Chloro-3-[(5-{N-(carboxamido)ethyl}pyrrolidin-2-yl)-([1,3,4]-oxadiazol-2-yl)]-1-(tetrahydropyran-4-yl)methyl-1H-indole The title compound was prepared using ethyl isocyanate. EsIMS: 480.0 m/z [M+Na]$^+$, $[\alpha]_D^{22}$ −40.0° (c=2.55 mg/ml in methanol).

EXAMPLE 18B (S)-7-Chloro-3-[(5-{N-cyclolropanesulfonyl}pyrrolidin-2-yl)-([1,3,4]-oxadiazol-2-yl)]-1-(tetrahydropyran-4-yl)methyl-1H-indole The title compound was prepared using cyclopropanesulfonyl chloride. EsIMS: 513.0 m/z [M+Na]$^+$, $[\alpha]_D^{22}$ −56.0° (c=1.0 mg/ml in methanol).

The following compound was prepared following the method of Example 18, using N-Boc-[D]-Proline instead of N-Boc-[L]-Proline.

EXAMPLE 18C (R)-7-Chloro-3-[(5-{N—(N',N'-dimethylsulfonamido)}pyrrolidin-2-yl)-([1,34]-oxadiazol-2-yl)]-1-(tetrahydropyran-4-yl)methyl-1H-indole The title compound was prepared using dimethylsulfamoylchloride. EsIMS: 516.0 m/z [M+Na]$^+$, $[\alpha]_D^{22}$+58.8° (c=1.40 mg/ml in methanol).

EXAMPLE 19

7-Chloro-3-[(5-{4-[(N-{2-hydroxylethyl)carboxamido]piperidin-1-yl}methyl)-([1,2,4]oxadiazol-3-yl)]-1-(tetrahydropyran-4-yl)methyl-1H-indole, hydrochloride salt Step A: 7-Chloro-1-(tetrahydropyran-4-yl)methyl-1H-indole-3-carbonitrile Phosphorus oxychloride (9.6 ml, 103 mmol) was added dropwise, via a pressure equalising funnel, to a cooled (5-10° C.) solution of 7-chloro-1-(tetrahydropyran-4-yl)methyl-1H-indole-3-carboxylic acid amide (20.0 g, 68.3 mmol) in dimethylformamide (200 ml). Following complete addition of phosphorus oxychloride the reaction was left to stir for 10 mins before warming to room temperature and allowing to stir for a further 30 mins. The reaction mixture was then poured carefully into ice cold water (2000 ml), the resulting precipitate filtered off and washed with water. The filter cake was then dissolved in dichloromethane, washed with water and brine, dried over sodium sulfate and the solvent removed in vacuo. The resulting solid was crystallised from diethyl ether to yield 7-chloro-1-(tetrahydropyran-4-yl)methyl-1H-indole-3-carbonitrile (12.9 g, 46.9 mmol) as a white solid.

Step B: 7-Chloro-1-(tetrahydropyran-4-yl)methyl-1H-indole-3-carboxamidine

To a suspension of 7-chloro-1-(tetrahydropyran-4-yl)methyl-1H-indole-3-carbonitrile (12.9 g, 46.9 mmol) in ethanol (280 ml) and di-iso-propylethylamine (16.7 ml, 96.0 mmol) was added hydroxylamine hydrochloride (6.8 g, 121.4 mmol). The reaction mixture was warmed to reflux and stirred for 6 h before cooling to room temperature and the solvent removed in vacuo. The solid was dissolved in dichloromethane washed with water and brine, dried over sodium sulfate and the solvent removed in vacuo. The resulting solid was crystallised from diethyl ether to yield 7-chloro-1-(tetrahydropyran-4-yl)methyl-1H-indole-3-carboxamidine (13.1 g, 42.5 mmol) as an off white solid.

Step C: 7-Chloro-3-[(5-chloromethyl)-([1,2,4]oxadiazol-3-yl)]-1-(tetrahydropyran-4-yl)methyl-1H-indole Molecular seives (5.3 g) were added to a stirred solution of 7-chloro-1-(tetrahydropyran-4-yl)methyl-1H-indole-3-carboxamidine (5.3 g, 17.2 mmol) in tetrahydrofuran (150 ml) and the reaction mixture was stirred for 60 mins. Sodium hydride (2.8 g, 116.6 mmol) was added portionwise and the reaction mixture allowed to stir for a further 60 mins before warming to 40° C. for 30 mins. The reaction was then cooled to −70° C. (dry ice/acetone bath) before the addition of chloroacetyl chloride (2.8 ml, 35.2 mmol) dropwise, via a pressure equalising funnel. The reaction was then allowed to warm to room temperature and stirred for a further 4 h before being quenched by the addition of water (5 ml), filtered and the solvent removed in vacuo. The solid was dissolved in dichloromethane, washed with water and brine, dried over sodium sulfate and the solvent removed in vacuo. The resulting residue was purified by flash column chromatography eluting with 1% (v/v) ethanol in dichloromethane through to 3% (v/v) ethanol in dichloromethane. The product containing fractions were combined, solvent removed in vacuo, and the resultant solid recrystallised from diethyl ether to yield 7-chloro-3-[(5-chloromethyl)-([1,2,4]oxadiazol-3-yl)]-1-(tetrahydropyran-4-yl)methyl-1H-indole (4.1 g, 11.2 mmol) as a white solid.

Step D: 7-Chloro-3-[(5-{4-[(N-{2-hydroxy}ethyl)carboxamido]piperidin-1-yl}methyl)-([1,2,4]oxadiazol-3-yl)]-1-(tetrahydropyran-4-yl)methyl-1H-indole To a solution of 7-chloro-3-[(5-chloromethyl)-([1,2,4]oxadiazol-3-yl)]-1-(tetrahydropyran-4-yl)methyl-1H-indole (0.25 g, 0.68 mmol) in acetonitrile (2 ml) was added piperidine-4-carboxylic acid (2-hydroxyethyl)amide (0.24 g, 1.36 mmol) and potassium carbonate (0.15 g, 1.05 mmol). The reaction was stirred at room temperature for 72 h before being diluted with dichloromethane (8 ml) and filtered through a 20 g Strata™ SCX giga tube. The tube was washed with methanol and then eluted with 2 M ammonia in methanol. The methanolic ammonia solution was evaporated to dryness. This was re-dissolved in dichloromethane, washed with sodium carbonate solution, water and brine, dried over sodium sulfate and the solvent removed in vacuo. The solid was dissolved in dichloromethane and hydrogen chloride (2 M solution in diethyl ether) was added. The resultant hydrochloride salt was precipitated from an ethanol and diethyl ether mixture to afford the title compound as a 1:1 hydrochloride salt (190 mg, 0.38 mmol). EsIMS: m/z 502.3 [M+H]$^+$.

EXAMPLE 20

7-Chloro-3-[(5-{[N-(carboxamido)methyl]-N-methylamino}methyl)-([1,2,4]oxadiazol-3-yl)]-1-(tetrahydropyran-4-yl)methyl-1H-indole, hydrochloride salt To a solution of 7-chloro-3-[(5-chloromethyl)-([1,2,4]oxadiazol-3-yl)]-1-(tetrahydropyran-4-yl)methyl-1H-indole (Example 19; Step C; 1.5 g, 4.09 mmol) in 1-methyl-2-pyrrolidinone (5 ml) was added N-methyl glycine amide hydrochloride (1.0 g, 8.19 mmol) and potassium carbonate (3.4 g, 24.6 mmol). The reaction was stirred at room temperature for 18 h before being diluted with dichloromethane (10 ml) and filtered through a 20 g Strata™ SCX giga tube. The tube was washed with methanol and then eluted with 2 M ammonia in methanol. The methanolic ammonia solution was evaporated to dryness. This was re-dissolved in dichloromethane, washed with water and brine, dried over sodium sulfate and the solvent removed in vacuo. The resulting residue was purified by flash column chromatography eluting with 2% (v/v) ethanol in dichloromethane. The solid was dissolved in dichloromethane and hydrogen chloride (2 M solution in diethyl ether) was added. The resultant hydrochloride salt was crystallised from acetone to afford the title compound as a 1:1 hydrochloride salt (1.24 g, 2.73 mmol). EsIMS: m/z 418.3 [M+H]$^+$.

EXAMPLE 20A

7-Chloro-3-({5-[(N-{[N-(carboxamido)methyl]carboxamido}methyl)-N-methylamino]methyl}-[1,2,4]oxadiazol-3-yl)-1-(tetrahydropyran-4-yl)methyl-1H-indole A solution of 7-Chloro-3-[(5-{[N-(carboxamido)methyl]-N-methylamino}methyl)-([1,2,4]oxadiazol-3-yl)]-1-(tetrahydropyran-4-yl)methyl-1H-indole, hydrochloride salt (1.19 g, 2.6 mmol) in dimethylformamide (15 ml) was cooled to 0° C. under nitrogen and sodium hydride (60% dispersion in mineral oil; 420 mg, 10.5 mmol) was added. The mixture was allowed to warm to room temperature and stirred at room temperature for 1 h. 2-Chloroacetamide (257 mg, 2.7 mmol) was then added and the mixture stirred for 4 days. The reaction mixture was filtered through a 20 g Strata™ SCX giga tube. The tube was washed with 10% methanol in dichloromethane and then eluted with 10% (2 M ammonia in methanol) in dichloromethane. The product was purified by column chromatography eluting with 5:95 (v/v) (2M ammonia in methanol): dichloromethane to give the title compound (32 mg, 0.07 mmol). EsIMS: m/z 475.3 [M+H]$^+$

EXAMPLE 20B

7-Chloro-3-({5-[(N-{[N-(2-hydroxyethyl)]carboxamido}methyl)-N-methylamino]methyl}-[1,2,4]oxadiazol-3-yl)-1-(tetrahydropyran-4-yl)methyl-1H-indole

Step A: 7-Chloro-3-({5-[(N-{methoxycarbonyl}methyl)-N-methylamino]methyl}-[1,2,4]oxadiazol-3-yl)-1-(tetrahydropyran-4-yl)methyl-1H-indole To a solution of 7-chloro-3-[(5-chloromethyl)-([1,2,4]oxadiazol-3-yl)]-1-(tetra-hydropyran-4-yl)methyl-1H-indole (Example 19; Step C; 1.0 g, 2.7 mmol) in acetonitrile (50 ml) was added sarcosine methyl ester hydrochloride (754 mg, 5.4 mmol) and di-isopropylethylamine (0.94 ml, 5.4 mmol). The mixture was heated at 60° C. with stirring for 18 h. The mixture was then concentrated in vacuo and the residue taken up in dichloromethane, washed with water, dried over sodium sulfate and the solvent removed in vacuo to afford 7-chloro-3-({5-[(N-{methoxycarbonyl}methyl)-N-methylamino]methyl}-[1,2,4]oxadiazol-3-yl)-1-(tetrahydropyran-4-yl)methyl-1H-indole as a brown oil (1.2 g, 2.7 mmol).

Step B: 7-Chloro-3-({5-[(N-{carboxyl}methyl)-N-methylamino]methyl}-[1,2,4]oxadiazol-3-yl)-1-(tetrahydropyran-4-yl)methyl-1H-indole To a solution of 7-chloro-3-({5-[(N-methoxycarbonyl}methyl)-N-methylamino]-methyl)[1,2,4]oxadiazol-3-yl)-1-(tetrahydropyran-4-yl)methyl-1H-indole (1.2 g, 2.7 mmol) in methanol (20 ml) and water (2 ml) was added sodium hydroxide (146 mg, 3.6 mmol). The mixture was heated at 60° C. with stirring for 2 h. The mixture was concentrated in vacuo and filtered through a 20 g Strata™ SCX giga tube. The tube was washed with methanol and then eluted with 2M ammonia in methanol to afford 7-chloro-3-({5-[(N-{carboxyl}methyl)-N-methylamino]methyl}-[1,2,4]oxadiazol-3-yl)-1-(tetrahydropyran-4-yl)methyl-1H-indole as a pale yellow powder (750 mg, 1.8 mmol).

Step C: 7-Chloro-3-({5-[(N-{[N-(2-hydroxyethyl)]carboxamido}methyl)-N-methylamino]methyl}-[1,2,4]oxadiazol-3-yl)-1-(tetrahydropyran-4-yl)methyl)-1H-indole To a suspension of 7-chloro-3-({5-[(N-{carboxyl}methyl)-N-methylamino]methyl}-[1,2,4]oxadiazol-3-yl)-1-(tetrahydropyran-4-yl)methyl-1H-indole (500 mg, 1.2 mmol) in dichloromethane (20 ml) was added di-isopropylethylamine (0.65 ml, 4.8 mmol) and ethanolamine (0.29 ml, 4.8 mmol). The mixture was cooled to 0° C. and 1-propylphosphonic acid cyclic anhydride (50% solution in ethyl acetate; 1.42 ml, 2.4 mmol) was added dropwise. The mixture was allowed to warm to room temperature and stirred for 1 h. The mixture was then diluted with dichloromethane (30 ml), washed with sodium carbonate solution (5% w/v in water; 50 ml), dried over sodium sulfate and the solvent removed. The residue was purified by flash column chromatography eluting with 2:98 (v/v) methanol: dichloromethane to give a colourless oil. Trituration with diethyl ether afforded the title compound as a white solid (269 mg, 0.6 mmol). EsIMS: m/z 462.1 [M+H]$^+$

EXAMPLE 21

(S)-7-Chloro-3-({5-[N-(1-carboxamido-2-hydroxyethyl)-N-methylamino]methyl}-[1,2,4]-oxadiazol-3-yl)-1-(tetrahydropyran-4-yl)methyl-1H-indole, hydrochloride salt A mixture of 7-chloro-3-[(5-chloromethyl)-([1,2,4]oxadiazol-3-yl)]-1-(tetrahydropyran-4-yl)methyl-1H-indole (Example 19; Step C; 29 mg, 0.08 mmol), sodium carbonate (9 mg, 0.09 mmol), sodium iodide (12 mg, 0.08 mmol) and N-methyl-L-serinamide (14 mg, 0.12 mmol) in acetonitrile (2 ml) was subjected to microwave irradiation at 160° C. for 5 mins. The reaction mixture was filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 50-100% (v/v) ethyl acetate in n-heptane, then 10% (v/v) methanol in ethyl acetate to give the free base of the title compound. Hydrochloride salt formation was achieved by the addition of hydrogen chloride (1 M solution in diethyl ether; 1 ml) to a solution of the free base in diethyl ether (5 ml). The mixture was concentrated in vacuo to afford the title compound as a 1:1 hydrochloride salt (24 mg). EsIMS: m/z 470.5 [M+Na]$^+$, 448.3 [M+H]$^+$, $[\alpha]_D^{22}$ +3.1° (c=2.75 mg/ml in methanol).

EXAMPLE 22

7-Chloro-3[(5-{[N-cyclopropylsulfonyl]-N-methylamino}methyl)-([1,2,4]-oxadiazol-3-yl)]-1-(tetrahydropyran-4-yl)methyl-1H-indole

Step A: 7-Chloro-3-[(5-{N-methylamino}methyl)-([1,2,4]-oxadiazol-3-yl)]-1-(tetrahydropyran-4-yl)methyl-1H-indole A mixture of 7-chloro-3-[(5-chloromethyl)-([1,2,4]oxadiazol-3-yl)]-1-(tetrahydropyran-4-yl)methyl-1H-indole (Example 19; Step C; 700 mg, 1.9 mmol), and 8 M methylamine in ethanol (5.0 ml, 40 mmol), in dichloromethane (50 ml) was stirred at 40° C. for 2 h. The reaction mixture was concentrated in vacuo and the obtained residue was purified by eluting with methanol and ammonia solution through a 5 g Strata™ SCX column. The mixture was concentrated in vacuo to afford 7-chloro-3-[(5-{N-methylamino}methyl)-([1,2,4]-oxadiazol-3-yl)]-1-(tetrahydropyran-4-yl)methyl-1H-indole (660 mg, 1.8 mmol) as a brown oil. EsIMS: 361.1 m/z [M+H]$^+$ Step B: Reaction with cyclopropanesulfonyl chloride according to the method described in example 18 afforded the title compound. EsIMS: 465.0 m/z [M+H]$^+$

EXAMPLE 22A

7-Chloro-3-[(5-{N—(N',N'-dimethylsulfonamido)}-N-methylamino}methyl)-(1,2,4]-oxadiazol-3-yl)]-1-(tetrahydropyran-4-yl)methyl-1H-indole The title compound was prepared according to the method of Example 22 using dimethylsulfamoylchloride. EsIMS: 489.9 m/z [M+Na]$^+$

EXAMPLE 23

7-Chloro-3-[(5-{[N-(formamido)ethyl]amino}methyl)-([1,2,4]-oxadiazol-3-yl)]-1-(tetrahydropyran-4-yl)methyl-1H-indole Step A: 7-Chloro-3-[(5-aminomethyl)-([1,2,4]-oxadiazol-3-yl)]-1-(tetrahydropyran-4-yl)methyl-1H-indole A mixture of 7-chloro-3-[(5-chloromethyl)-([1,2,4]oxadiazol-3-yl)]-1-(tetrahydropyran-4-yl)methyl-1H-indole (Example 19; Step C; 500 mg, 1.4 mmol), and 2 M ammonia in methanol (3.0 ml, 6.0 mmol) was subjected to microwave irradiation at 120° C. for 20 mins using an Emrys Optimizer EXP™. The reaction mixture was concentrated in vacuo and the obtained residue was purified by eluting with methanol and ammonia solution through a 5 g Strata™ SCX column. The mixture was concentrated in vacuo and dissolved in dichloromethane (1 ml) to which 2M HCl in diethyl ether was added to yield 7-chloro-3-[(5-aminomethyl)-([1,2,4]-oxadiazol-3-yl)]-1-(tetrahydropyran-4-yl)methyl-1H-indole (500 mg, 1.8 mmol) as the hydrochloride salt. EsIMS: 347 m/z [M+H]$^+$ Step B: Reaction with ethyl isocyanate according to the method described in example 18 afforded the title compound. EsIMS: 418.1 m/z [M+H]$^+$

EXAMPLE 24

7-Chloro-3-[(5-{[N-methoxymethylformyl]amino}methyl)-([1,2,4]-oxadiazol-3-yl)]-1-(tetrahydropyran-4-yl)methyl-1H-indole A mixture 7-chloro-3-[(5-aminomethyl)-([1,2,4]-oxadiazol-3-yl)]-1-(tetrahydropyran-4-yl)methyl-1H-indole hydrochloride salt (prepared as in Example 23) (50 mg, 0.14 mmol), O-benzotriazol-1-yl-N,N,N',N'-tetramethyluronium hexafluoro-phosphate (53 mg, 2.1 mmol), di-iso-propylethylamine (51 µl, 9.1 mmol) and methoxyacetic acid (15 µl, 0.15 mmol) in dichloromethane (10 ml) was stirred at room temperature for 16 h. The organics were washed with 2M aqueous HCl solution (20 ml), dried over magnesium sulfate, filtered, and the solvent removed in vacuo. Purified by semi-prep. HPLC (Method i) to title compound (10 mg, 0.024 mmol) as a solid. EsIMS: 419.1 m/z [M+H]$^+$

EXAMPLE 25

7-Chloro-3-[(5-{N—(N',N'-dimethylsulfonamido)}-(N-{2-hydroxy}ethylamino)methyl)-([1,2,4]-oxadiazol-3-yl)]-1-(tetrahydropyran-4-yl)methyl-1H-indole A mixture of 7-chloro-3-[(5-chloromethyl)-([1,2,4]oxadiazol-3-yl)]-1-(tetrahydropyran-4-yl)methyl-1H-indole (Example 19; Step C; 500 mg, 1.4 mmol), and 2-ethanolamine (0.5 ml, 8.0 mmol) in dichloromethane (3 ml) was subjected to microwave irradiation at 100° C. for 60 mins using an Emrys Optimizer EXP™. The reaction mixture was concentrated in vacuo and the obtained residue was purified by eluting with methanol and ammonia solution through a 5 g Strata™ SCX column to yield 180 mg of a yellow liquid. The residue was mixed with trimethylsilyl chloride (63 µl, 0.51 mmol), imidazole (35 mg, 0.51 mmol), and dimethylaminopyridine (2 mg, 0.018 mmol) for 30 mins at room temperature. Water (5 ml) was added and the reaction concentrated in vacuo. A mixture of the residue and di-iso-propylethylamine (63 µl, 0.48 mmol), dimethylsulfamoylchloride chloride (20 µl, 0.27 mmol) and dimethylaminopyridine (2 mg, 0.018 mmol) in dichloromethane (10 ml) was left to stir at room temperature for 16 h. The organics were washed with 2M aqueous HCl solution (20 ml), dried over magnesium sulfate, filtered, and the solvent removed in vacuo. Purified by semi-prep. HPLC (Method i) to afford the title compound (10 mg, 0.020 mmol) as a solid. EsIMS: 498.1 m/z [M+H]$^+$

EXAMPLE 26

In-Vitro Determination of Efficacy And Potency At the Human CB1 Receptor Expressed in CHO Cells Chinese Hamster Ovary (CHO) cells expressing the human CB1 receptor and a luciferase reporter gene were suspended in phenol red/serum free DMEM/F-12 nut mix containing penicillin/streptomycin (50U/50 µg/ml) and fungizone (1 µg/ml) and seeded into 96 well plates at a density of $3 \times 10^4$ cells per well (100 µl final volume). Cells were incubated overnight (approx. 18 h at 37° C., 5% CO$_2$/95% air) prior to assay. The test compound (10 mM solution in dimethylsulfoxide) was diluted in F12 Nut Mix to give a range of stock solutions from 0.11 mM to 0.11 nM. The stock solutions (10 µl) were added directly to the relevant wells. The plates were incubated at 37° C. for 5 h to allow agonist-induced expression of the luciferase enzyme. Under subdued light, LucLite substrate (Packard; reconstituted as per manufacturer's instructions; 100 µl) was added to each well. Plates were covered with Top Seal and then incubated at room temperature for 5 minutes before counting on the Packard TopCount (single photon counting, 0.01 minute count time, 5 minute count delay). A "best-fit" curve was fitted by a minimum sum of squares method to the plot of counts per second (CPS) against compound concentration (M) to obtain an EC$_{50}$ value. Table 1 shows the pEC$_{50}$ values obtained for some representative compounds of the invention.

TABLE 1

| Example | Chemical name | Chemical structure | pEC$_{50}$ |
|---|---|---|---|
| 7 | 7-Chloro-3-({5-[(N-{2-methoxy}ethyl)-(N-{methylsulfonyl})amino]methyl}-([1,2,4]-thiadiazol-3-yl))-1-(tetrahydropyran-4-yl)methyl-1H-indole | 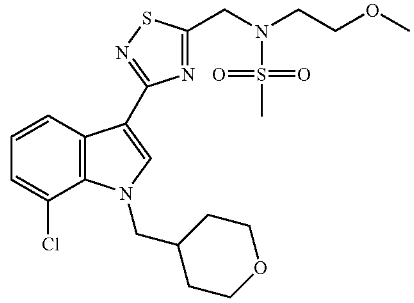 | 7.1 |
| 9 | 7-Ethyl-3-[(5-{[N-(carboxamido)methyl]-N-methylamino}methyl)-([1,2,4]-thiadiazol-3-yl)]-1-(tetrahydropyran-4-yl)-methyl-1H-indole, hydrochloride acid salt | 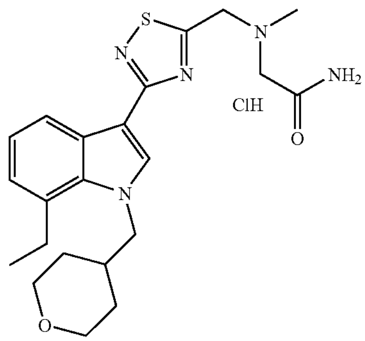 | 6.9 |
| 10A | 7-Ethyl-3-[(5-{4-[(N-{2-hydroxy}ethyl)-carboxamido]piperidin-1-yl}methyl)-([1,2,4]-thiadiazol-3-yl)]-1-(tetrahydropyran-4-yl)methyl-1H-indole | 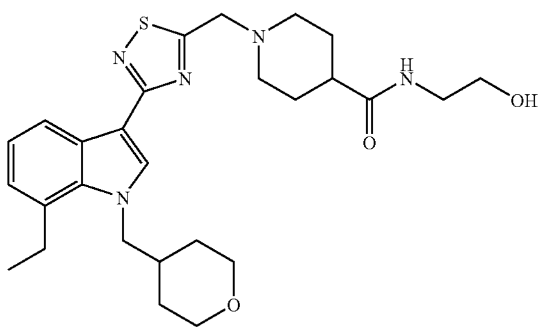 | 7.9 |
| 12 | 7-Ethyl-3-[(5-{[N-(2,3-dihydroxypropyl)]-methylamino}methyl)-([1,2,4]-thiadiazol-3-yl)]-1-(tetrahydropyran-4-yl)methyl-1H-indole, | 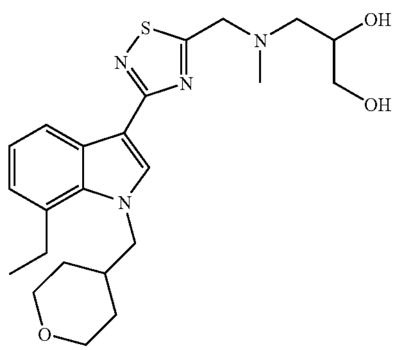 | 6.9 |

TABLE 1-continued

| Example | Chemical name | Chemical structure | pEC$_{50}$ |
|---|---|---|---|
| 13 | 7-Chloro-3-[(5-{[4-(N-methyl)carbox-amido]piperidin-1-yl}methyl)-([1,2,4]-thiadiazol-3-yl)]-1-(1,1-dioxo-hexahydro-thiopyran-4-yl)methyl-1H-indole, hydrochloride salt | 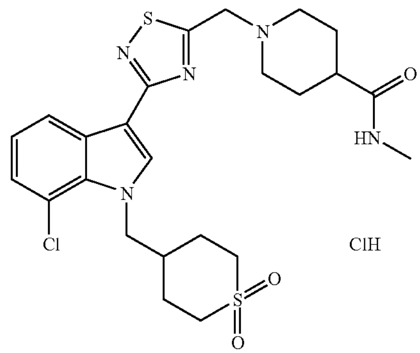 | 6.9 |
| 15 | 7-Chloro-3-({5-[(N-{2-hydroxy}ethyl)-(N-{methylsulfonyl})amino]methyl}-([1,2,4]-thiadiazol-3-yl))-1-(tetrahydropyran-4-yl)methyl-1H-indole | 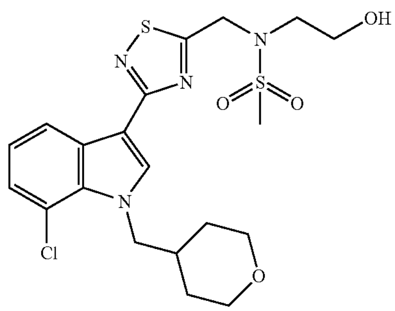 | 7.7 |
| 17 | 7-Chloro-3-[(5-{4-[hydroxymethyl]-piperidin-1-yl}methyl)-([1,3,4]-oxadiazol-2-yl)]-1-(cyclohexyl)methyl-1H-indole, hydrochloride salt | 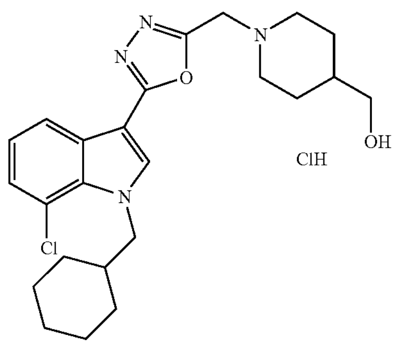 | 6.9 |
| 18 | (S)-7-Chloro-3-[(5-{N-cyclopropane-sulfonyl}pyrrolidin-2-yl)-([1,3,4]-oxadiazol-3-yl)]-1-(tetrahydropyran-4-yl)-methyl-1H-indole | 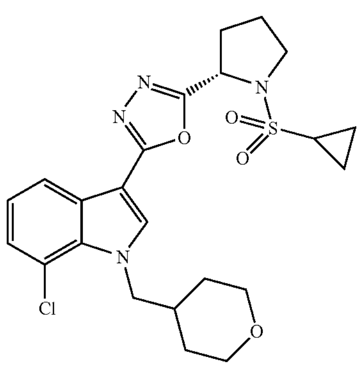 | 7.2 |

TABLE 1-continued

| Example | Chemical name | Chemical structure | pEC$_{50}$ |
|---|---|---|---|
| 19 | 7-Chloro-3-[(5-{4-[(N-{2-hydroxy}ethyl)-carboxamido]piperidin-1-yl}methyl)-([1,2,4]oxadiazol-3-yl)]-1-(tetrahydro-pyran-4-yl)methyl-1H-indole, hydrochloride salt | 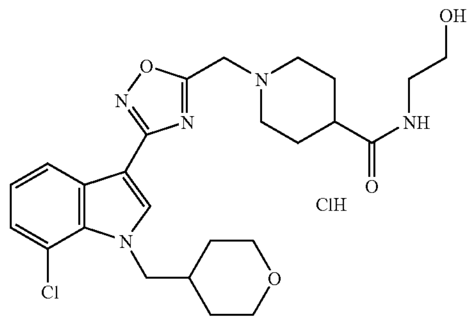 | 7.1 |
| 20 | 7-Chloro-3-[(5-{[N-(carboxamido)-methyl]-N-methylamino}methyl)-([1,2,4]-oxadiazol-3-yl)]-1-(tetrahydropyran-4-yl)methyl-1H-indole, hydrochloride salt | 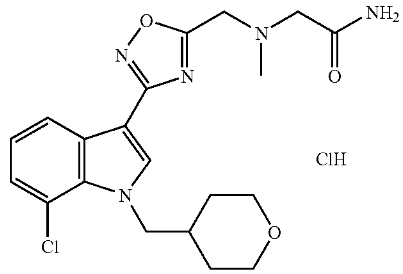 | 7.4 |
| 20A | 7-Chloro-3-({5-[(N-{[N-(carboxamido)methyl]carboxamido}-methyl)-N-methylamino]methyl}-[1,2,4]oxadiazol-3-yl)-1-(tetrahydropyran-4-yl)methyl-1H-indole | 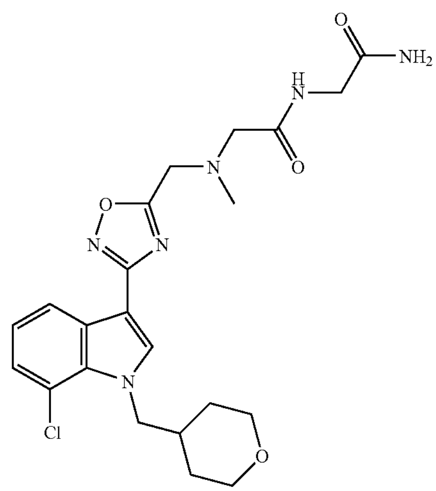 | 7.5 |
| 20B | 7-Chloro-3-({5-[(N-{[N-(2-hydroxyethyl)]carboxamido}methyl)-N-methylamino]methyl}-[1,2,4]oxadiazol-3-yl)-1-(tetrahydropyran-4-yl)methyl-1H-indole | 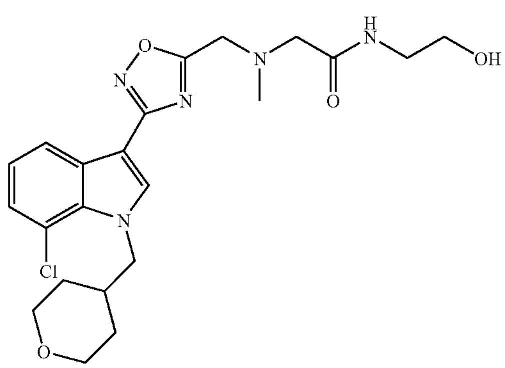 | 7.3 |

TABLE 1-continued

| Example | Chemical name | Chemical structure | pEC$_{50}$ |
|---|---|---|---|
| 24 | 7-Chloro-3-[(5-{[N-methoxymethyl-formyl]amino}methyl)-([1,2,4]-oxadiazol-3-yl)]-1-(tetrahydropyran-4-yl)methyl-1H-indole | 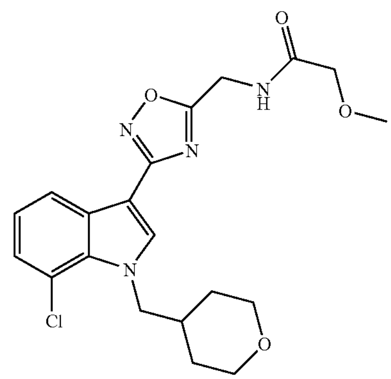 | 6.7 |
| 25 | 7-Chloro-3-[(5-{N-(N',N'-dimethylsulfonamido)}-(N-{2-hydroxy}ethylamino)-methyl)-([1,2,4]-oxadiazol-3-yl)]-1-(tetrahydropyran-4-yl)methyl-1H-indole | 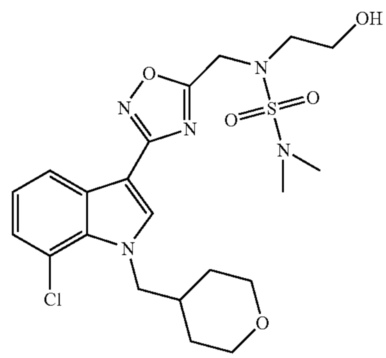 | 7.0 |

EXAMPLE 27

Formalin Paw Test In Mice

Four-six groups of six mice were treated with vehicle and one of four to five doses of the test compound (typically between 0.03, 0.1, 3 and 10 μmol/kg), administered intravenously into the tail vein (vehicle: 10% Tween-80 in saline; injection volume 10 ml/kg). This injection was followed 5 minutes later by 20 μl of 5% formalin, which was administered sub-cutaneously to the dorsum of the left hind paw. Immediately after formalin administration the animal was placed in a test chamber and data acquisition, using a detection device (Automated Nociception Analyser (ANA); Department of Anesthesiology, University of California, San Diego), was started, independently for each chamber. The nociceptive behaviour was measured as the number of counts (licking, lifting, biting and flinching actions) detected within the two phases of nociception (Yaksh et al, 2001). The nociceptive behaviour between 0 and 5 min after formalin injection (Phase 1) and between 20 and 30 min after formalin injection (Phase 2) was recorded and number of counts for each mouse, compared to the mean number of counts for the vehicle treated animals, was calculated. Once values for each mouse were obtained, the mean and s.e.m. were calculated for each treatment group. The percent inhibition data were then used to calculate ED$_{50}$ values for Phase 1 and Phase 2.

The compounds of examples 10A, 15, 19 and 20 inhibited the nociceptive behaviour of Phase 2 at an ED$_{50}$<5 μmol/kg.

The invention claimed is:

1. An indole having the general Formula I

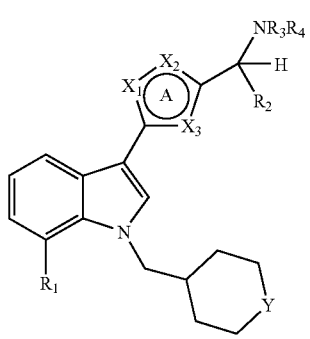

Formula I wherein

A represents a 5-membered aromatic heterocyclic oxadiazole or thiadiazole ring, wherein $X_1$, $X_2$ and $X_3$ are independently selected from N, O, and S;

Y is $CH_2$, O, S or $SO_2$;

$R_1$ is $(C_{1-4})$alkyl, $(C_{1-4})$alkyloxy, CN or halogen;

$R_2$ is H or $(C_{1-4})$alkyl; or $R_2$ together with $R_3$ and the carbon and nitrogen atoms to which they are bonded form pyrrolidine;

$R_3$ is H, $(C_{1-6})$alkyl or $(C_{3-7})$cycloalkyl, the alkyl groups being optionally substituted with OH, $(C_{1-4})$alkyloxy, $(C_{1-4})$alkylthio, $(C_{1-4})$alkylsulfonyl, CO—NR$_5$R$_6$, CO—OR$_7$, CN or halogen;

$R_4$ is CO—$NR_5R_6$, CO—$OR_5$, $SO_2$—$R_8$, $SO_2$—$NR_9R_{10}$, or CO—$R_{11}$; or $R_4$ is $(C_{1-3})$alkyl, substituted with CO—$NR_5R_6$, CO—$OR_7$, $SO_2$—$R_8$, $SO_2$—$NR_9R_{10}$, NH—CO—$R_{11}$, NH—$SO_2$—$R_{12}$, or two OH groups; and optionally further substituted with OH; or $R_4$ together with $R_3$ and the N to which they are bonded form a 4-8 membered ring optionally containing a further heteroatom selected from O, S and $SO_2$, the ring being substituted with CO—$NR_{13}R_{14}$, CO—$OR_7$, $SO_2$—$R_8$, $SO_2$—$NR_9R_{10}$, NH—CO—$R_{11}$ or NH—$SO_2$—$R_{12}$; or the ring being substituted with $(C_{1-3})$alkyl, substituted with NH—CO—$R_{11}$ or NH—$SO_2$—$R_{12}$;

$R_5$, when present, is H or $(C_{1-4})$alkyl, optionally substituted with OH, $(C_{1-4})$alkyloxy or $CONR_7R_8$;

$R_6$, when present, is H or $(C_{1-4})$alkyl; or $R_6$ together with $R_5$ and the N to which they are bonded form a 4-8 membered ring optionally containing a further heteroatom selected from O, S and $SO_2$, the ring being optionally substituted with OH;

$R_7$, when present, is H or $(C_{1-4})$alkyl;

$R_8$, when present, is $(C_{1-4})$alkyl or $(C_{3-7})$cycloalkyl, optionally substituted with OH or $(C_{1-4})$alkyloxy;

$R_9$, when present, is H or $(C_{1-4})$alkyl, optionally substituted with OH or $(C_{1-4})$alkyloxy;

$R_{10}$, when present, is H or $(C_{1-4})$alkyl;

$R_{11}$, when present, is H or $(C_{1-4})$alkyl, optionally substituted with OH or $(C_{1-4})$alkyloxy;

$R_{12}$, when present, is $(C_{1-4})$alkyl, optionally substituted with OH or $(C_{1-4})$alkyloxy;

$R_{13}$, when present, is H or $(C_{1-4})$alkyl, optionally substituted with OH, $(C_{1-4})$alkyloxy or $CONR_7R_8$;

$R_{14}$, when present, is H or $(C_{1-4})$alkyl; or $R_{14}$ together with the C atom to which the CO—$NR_{13}R_{14}$ group is bonded form a 5- or 6-membered spiro-ring;

with the proviso that when Y is $SO_2$, $R_4$ may further represent H, $(C_{1-6})$alkyl or $(C_{3-7})$cycloalkyl, the alkyl groups being optionally substituted with OH, $(C_{1-4})$alkyloxy, $(C_{1-4})$alkylthio, $(C_{1-4})$alkylsulfonyl, CN or halogen; or $R_3$ together with $R_4$ and the N to which they are bonded may form a 4-8 membered ring optionally containing a further heteroatom selected from O, S and $SO_2$ the ring being optionally substituted with OH;

or a pharmaceutically acceptable salt thereof.

2. The indole of claim 1, wherein

R, when present, is H;

Y is $CH_2$, O or $SO_2$;

$R_2$ is H; or $R_2$ together with $R_3$ and the carbon and nitrogen atoms to which they are bonded form a 5-membered ring.

3. The indole of claim 1, wherein $X_1$ is N or S;

$X_2$ is S, O, or N;

$X_3$ is N or O.

4. The indole of claim 3, wherein the heterocycle A is 1,2,4-oxadiazole ($X_1$ is N, $X_2$ is O, $X_3$ is N), 1,2,4-thiadiazole ($X_1$ is N, $X_2$ is 5, $X_3$ is N), thiazole ($X_1$ is S, $X_2$ is CR, $X_3$ is N) or 1,3,4-oxadiazole ($X_1$ is N, $X_2$ is N, $X_3$ is O).

5. The indole of claim 4, wherein the heterocycle A is 1,2,4-oxadiazole ($X_1$ is N, $X_2$ is O, $X_3$ is N) or 1,2,4-thiadiazole ($X_1$ is N, $X_2$ is 5, $X_3$ is N).

6. The indole of claim 5, wherein $R_3$ is $(C_{1-6})$alkyl, optionally substituted with OH;

$R_4$ is $SO_2$—$R_8$; or $R_4$ is $(C_{1-3})$ alkyl, substituted with CO—$NR_5R_6$; or $R_4$ together with $R_3$ and the N to which they are bonded form a 6-membered ring, the ring being substituted with CO—$NR_{13}R_{14}$.

7. The indole of claim 1 which is selected from

7-Chloro-3-[(5-{[4-(N-methyl)carboxamido]piperidin-1-yl}methyl)-([1,2,4]-thiadiazol-3-yl)]-1-(1,1-dioxo-hexahydro-thiopyran-4-yl)methyl-1H-indole;

7-Chloro-3-[(5-{4-[(N-{2-hydroxy}ethyl)carboxamido]piperidin-1-yl}methyl)-([1,2,4]oxadiazol-3-yl)]-1-(tetrahydropyran-4-yl)methyl-1H-indole;

7-Chloro-3-[(5-{[N-(carboxamido)methyl]-N-methylamino}methyl)-([1,2,4]oxadiazol-3-yl)]-1-(tetrahydropyran-4-yl)methyl-1H-indole;

7-Chloro-3-({5-[(N—{[N-(carboxamido)methyl]carboxamido}methyl)-N-methyl-amino]methyl}-[1,2,4]oxadiazol-3-yl)-1-(tetrahydropyran-4-yl)methyl-1H-indole;

7-Chloro-3-({5-[(N—{[N-(2-hydroxyethyl)]carboxamido}methyl)-N-methylamino]methyl}-[1,2,4]oxadiazol-3-yl)-1-(tetrahydropyran-4-yl)methyl-1H-indole;

7-Chloro-3-({5-[(N-{2-hydroxy}ethyl)-(N-{methylsulfonyl})amino]methyl}-([1,2,4]-thiadiazol-3-yl))-1-(tetrahydropyran-4-yl)methyl-1H-indole; and 7-Ethyl-3-[(5-{4-[(N-{2-hydroxy}ethyl)carboxamido]piperidin-1-yl}methyl)-([1,2,4]-thiadiazol-3-yl)]-1-(tetrahydropyran-4-yl)methyl-1H-indole;

or a pharmaceutically acceptable salt thereof.

8. A pharmaceutical composition comprising an indole of claim 1 in admixture with pharmaceutically acceptable auxiliaries.

9. A pharmaceutical composition comprising an indole of claim 5 in admixture with pharmaceutically acceptable auxiliaries.

10. A pharmaceutical composition comprising an indole of claim 6 in admixture with pharmaceutically acceptable auxiliaries.

11. A pharmaceutical composition comprising an indole of claim 7 in admixture with pharmaceutically acceptable auxiliaries.

12. A method of treatment of pain comprising:
administering to a patient in need thereof a therapeutically effective amount of an indole derivative of claim 1.

13. The method according to claim 12, wherein the pain is selected from the group consisting of peri-operative pain, chronic pain, neuropathic pain, cancer pain and pain and spasticity associated with multiple sclerosis.

14. A method of treatment of pain comprising: administering to a patient in need thereof a therapeutically effective amount of an indole derivative of claim 5.

15. A method of treatment of pain comprising: administering to a patient in need thereof a therapeutically effective amount of an indole derivative of claim 6.

16. A method of treatment of pain comprising: administering to a patient in need thereof a therapeutically effective amount of an indole derivative of claim 7.

\* \* \* \* \*